US008017315B2

(12) United States Patent
Kufe

(10) Patent No.: US 8,017,315 B2
(45) Date of Patent: Sep. 13, 2011

(54) MITOCHONDRIAL LOCALIZATION OF MUC1

(75) Inventor: Donald W. Kufe, Wellesley, MA (US)

(73) Assignee: Dana Farber Cancer Institute, Inc., Boston, MA (US)

( * ) Notice: Subject to any disclaimer, the term of this patent is extended or adjusted under 35 U.S.C. 154(b) by 342 days.

(21) Appl. No.: 12/064,425

(22) PCT Filed: Aug. 21, 2006

(86) PCT No.: PCT/US2006/032906
§ 371 (c)(1),
(2), (4) Date: Jul. 8, 2008

(87) PCT Pub. No.: WO2007/024940
PCT Pub. Date: Mar. 1, 2007

(65) Prior Publication Data
US 2009/0136520 A1 May 28, 2009

Related U.S. Application Data

(60) Provisional application No. 60/710,166, filed on Aug. 22, 2005.

(51) Int. Cl.
*C12Q 1/00* (2006.01)
*G01N 33/53* (2006.01)
*C07K 14/00* (2006.01)
(52) U.S. Cl. ............ 435/4; 435/7.1; 435/7.21; 530/300; 530/324; 530/350
(58) Field of Classification Search ........................ None
See application file for complete search history.

(56) References Cited

U.S. PATENT DOCUMENTS

| | | | |
|---|---|---|---|
| 4,918,166 A | 4/1990 | Kingsman et al. | 530/350 |
| 5,597,457 A | 1/1997 | Craig et al. | 204/165 |
| 5,790,421 A | 8/1998 | Osslund | 703/2 |
| 6,093,573 A | 7/2000 | Beamer et al. | 436/86 |
| 7,247,297 B2 | 7/2007 | Weichselbaum et al. | 424/93.2 |
| 7,745,109 B2 * | 6/2010 | Kufe | 435/4 |
| 2002/0041868 A1 | 4/2002 | Nicolette et al. | 424/93.21 |
| 2002/0110841 A1 * | 8/2002 | Kufe | 435/7.23 |
| 2003/0105000 A1 * | 6/2003 | Pero et al. | 514/12 |
| 2004/0018181 A1 | 1/2004 | Kufe et al. | 424/93.21 |
| 2004/0166543 A1 | 8/2004 | Kufe | 435/7.23 |
| 2005/0015232 A1 | 1/2005 | Reinherz et al. | 703/11 |
| 2005/0042209 A1 | 2/2005 | Kufe et al. | 424/93.21 |
| 2005/0053606 A1 | 3/2005 | Kufe et al. | 424/155.1 |
| 2005/0169898 A1 | 8/2005 | Gong et al. | 424/93.21 |
| 2005/0238627 A1 | 10/2005 | Ohno et al. | 424/93.21 |
| 2007/0105767 A1 | 5/2007 | Kharbanda et al. | 514/12 |
| 2007/0141704 A1 | 6/2007 | Nicolette et al. | 435/455 |
| 2007/0202134 A1 | 8/2007 | Kufe et al. | 424/277.1 |

FOREIGN PATENT DOCUMENTS

| | | |
|---|---|---|
| EP | 0184187 | 6/1986 |
| WO | WO 87/02671 | 5/1987 |
| WO | WO 00/09744 | 3/2000 |
| WO | WO 00/11206 | 3/2000 |
| WO | WO 00/47763 | 8/2000 |
| WO | WO 2005-042573 | 5/2005 |

OTHER PUBLICATIONS

Bowie et al (Science, 1990, 247:1306-1310).*
Skolnick et al. (TIBTECH 18:34-39, 2000).*
Ibragimova and Eade (Biophysical Journal, Oct. 1999, vol. 77, pp. 2191-2198).*
Burgess et al (J. of Cell Bio. 111:2129-2138, 1990).*
Lazar et al (Molecular and Cellular Biology, 1988, 8:1247-1252).*
Scott et al. (Nature Genetics, 1999, 21:440-443).*
International Search Report and Written Opinion, issued in International Application No. PCT/US06/32906, dated Jul. 11, 2008.
Baldus et al.,"MUC1 and nuclear beta-catenin are coexpressed at the invasion front of colorectal carcinomas and are both correlated with tumor prognosis," *Clin. Cancer Res.*, 10:2790-2796, 2004.
Barrios et al., "Mycobacterial heat-shock proteins as carrier molecules. II: The use of the 70-kDa mycobacterial heat-shock protein as carrier for conjugated vaccines can circumvent the need for adjuvants and Bacillus Calmette Guérin priming," *Eur. J. Immunol.*, 22:1365-1372, 1992.
Belsches-Jablonski et al., "Src family kinases and HER2 interactions in human breast cancer cell growth and survival," *Oncogene*, 20:1465-1475, 2001.
Brody et al., "Aptamers as therapeutic and diagnostic agents," *Reviews in Molecular Biotechnology*, 74:5-13, 2000.
Broughton, "Molecular modeling," *Curr. Opin. Chem. Biol.*, 1:392-398, 1997.
Bukau et al., "Getting newly synthesized proteins into shape," *Cell*, 101:119-122, 2000.
Cohen et al., "Molecular modeling software and methods for medicinal chemistry," *J. Med. Chem.*, 33:883-894, 1990.
Crisitano et al., "Molecular conjugates: a targeted gene delivery vector for molecular medicine," *J. Mol. Med.*, 73:479, 1995.
Croce et al., "Patterns of MUC1 tissue expression defined by an anti-MUC1 cytoplasmic tail monoclonal antibody in breast cancer," *J. Histochem. Cytochem.*, 51:781-8, 2003.
Datta et al., "XIAP regulates DNA damage-induced apoptosis downstream of caspase-9 cleavage.," *J. Biol. Chem.*, 275:31733-31738, 2000.
Gendler et al., "A highly immunogenic region of a human polymorphic epithelial mucin expressed by carcinomas is made up of tandem repeats," *J. Biol.Chem.*, 263:12820-12823, 1988.
Hartl & Hayer-Hartl, "Molecular chaperones in the cytosol: from nascent chain to folded protein," *Science*, 295:1852-1858, 2002.
Huang et al., "MUC1 cytoplasmic domain coactivates Wnt target gene transcription and confers transformation," *Cancer Biol. Ther.*, 2:702-706, 2003.
Hudson et al., "High avidity scFv multimers; diabodies and triabodies," *J. Immunol. Methods*, 23:(1-2):177-189, 1999.
Huston et al., "Engineered antibodies take center stage," *Hum. Antibodies*, 10(3-4):127-142, 2001.

(Continued)

*Primary Examiner* — Peter J Reddig
(74) *Attorney, Agent, or Firm* — Fulbright & Jaworski

(57) ABSTRACT

The invention provides methods of identifying and making compounds that inhibit the interaction between MUC1 and either or both of HSP70 and HSP90. Also embraced by the invention are in vivo and in vitro methods of inhibiting such an interaction.

7 Claims, 19 Drawing Sheets

OTHER PUBLICATIONS

Kharbanda et al., "Nuclear signaling induced by ionizing radiation involves colocalization of the activated p56/p53lyn tyrosine kinase with p34cdc2," *Cancer Res.*, 56:3617-3621, 1996.

Kinlough et al., "MUC1 membrane trafficking is modulated by multiple interactions," *J. Biol. Chem.*, 279:53071-53077, 2004.

Kufe et al., "Differential reactivity of a novel monoclonal anitbody (DF3) with human malignant versus benign breat tumors," *Hybridoma*, 3:223-232, 1984.

Levitin et al., "The MUC1 SEA module is a self-cleaving domain," *J. Biol. Chem.*, 2005.

Li et al., "Interaction of glycogen synthase kinase 3beta with the DF3/MUC1 carcinoma-associated antigen and beta-catenin," *Mol. Cell. Bio.*, 18:7216-7224, 1998.

Li et al., "The c-Src tyrosine kinase regulates signaling of the human DF3/MUC1 carcinoma-associated antigen with GSK3 beta and beta-catenin," *J. Biol. Chem.*, 276:6061-6064, 2001.

Li et al., "The epidermal growth factor receptor regulates interaction of the human DF3/MUC1 carcinoma antigen with c-Src and beta-catenin," *J. Biol. Chem.*, 276:35239-35242, 2001.

Li et al., "DF3/MUC1 signaling in multiple myeloma cells is regulated by interleukin-7," *Cancer Biol. Ther.*, 2:187-193, 2003.

Li et al., "Human DF3/MUC1 carcinoma-associated protein functions as an oncogene," *Oncogene*, 22:6107-6110, 2003.

Li et al., "Heregulin targets gamma-catenin to the nucleolus by a mechanism dependent on the DF3/MUC1 oncoprotein," *Mol. Cancer Res.*, 1:765-775, 2003.

Ligtenberg et al., "Cell-associated episialin is a complex containing two proteins derived from a common precursor," *J. Bio. Chem.*, 267:6171-7, 1992.

McPherson, "Crystallization of proteins from polyethylene glycol," *J. Biol. Chem.*, 251:6300-6306, 1976.

Merlo et al., "Frequent alteration of the DF3 tumor-associated antigen gene in primary human breast carcinomas.," *Cancer Res.*, 49:6966-6971, 1989.

Moro et al., "The TIM17.23 preprotein translocase of mitochondria: composition and function in protein transport into the matrix," *EMBO J.*, 18:3667-75, 1999.

Navia et al., "Use of structural information in drug design," *Curr. Opin. Struct. Biol.*, 2:202-210, 1992.

Ng et al., "p28 Bap31, a Bcl-2/Bcl-XL- and procaspase-8-associated protein in the endoplasmic reticulum," *J. Cell Biol.*, 139:327-38, 1997.

Perey et al., "Tumor selective reactivity of a monoclonal antibody prepared against a recombinant peptide derived from the DF3 human breast carcinoma-associated antigen," *Cancer Res.*, 52:2536-2568, 1992.

Poljak, "Production and structure of diabodies," *Structure* 2(12):1121-1123, 1994.

Rahn et al., "The importance of MUC1 cellular localization in patients with breast carcinoma: an immunohistologic study of 71 patients and review of the literature," *Cancer*, 91:1973-82, 2001.

Ramanathan et al., "Phase I study of a MUC1 vaccine composed of different doses of MUC1 peptide with SB-AS2 adjuvant in resected and locally advanced pancreatic cancer," *Cancer Immunol. Immunother.*, 54:254-264, 2005.

Ren et al., "Protein kinase C delta regulates function of the DF3/MUC1 carcinoma antigen in beta-catenin signaling," *J. Biol. Chem.*, 277:17616-17622, 2002.

Ren et al., "Human MUC1 carcinoma-associated protein confers resistance to genotoxic anticancer agents," *Cancer Cell*, 5:163-175, 2004.

Ryan et al., "Assaying protein import into mitochondria," *Methods Cell Biol.*, 65:189-215, 2001.

Schreiber et al., "Binding of tumor antigen mucin (MUC1) derived peptides to the heat shock protein DnaK," *Anticancer Research*, 20: 3093-3098, 2000.

Schroeder et al., "Transgenic MUC1 interacts with epidermal growth factor receptor and correlates with mitogen-activated protein kinase activation in the mouse mammary gland," *J. Biol. Chem.*, 276:13057-13064, 2001.

Schroeder et al., "MUC1 overexpression results in mammary gland tumorigenesis and prolonged alveolar differentiation," *Oncogene*, 23:5739-5747, 2004.

Siddiqui et al., "Isolation and sequencing of a cDNA coding for the human DF3 breast carcinoma-associated antigen," *Proc. Natl. Acad. Sci USA*, 85:2320-2323, 1988.

Stocks, "Intrabodies: production and promise," *Drug. Discov. Today*, 9(22):960-966, 2004.

Truscott et al., "Mechanisms of protein import into mitochondria," *Curr. Biol.*, 13:R326-37, 2003.

Vadlamudi et al., "Heregulin and HER2 signaling selectively activates c-Src phosphorylation at tyrosine 215," *FEBS Lett.*, 543:76-80, 2003.

Wada & Kanwar, "Characterization of mammalian translocase of inner mitochondrial membrane (Tim44) isolated from diabetic newborn mouse kidney," *Proc. Natl. Acad. Sci USA*, 95:144-9, 1998.

Wei et al., "Human MUC1 oncoprotein regulates p53-responsive gene transcription in the genotoxic stress response," *Cancer Cell*, 7:167-178, 2005.

Wen et al., "Nuclear association of the cytoplasmic tail of MUC1 and beta-catenin," *J. Biol. Chem.*, 278:38029-39, 2003.

Wheeler et al., "Intrabody and intrakine strategies for molecular therapy," *Mol. Ther.* 8(3):355-366, 2003.

Whitesell et al., "Inhibition of heat shock protein HSP90-pp60v-src heteroprotein complex formation by benzoquinone ansamycins: essential role for stress proteins in oncogenic transformation," *Proc. Natl. Acad. Sci. USA*, 91:8324-8, 1994.

Yamamoto et al., "Interaction of the DF3/MUC1 breast carcinoma-associated antigen and beta-catenin in cell adhesion," *J. Biol. Chem.*, 272:12492-12494, 1997.

Young & Hartl, "Polypeptide release by Hsp90 involves ATP hydrolysis and is enhanced by the co-chaperone p23," *EMBO J.*, 19:5930-40, 2000.

Young et al., "Molecular chaperones Hsp90 and Hsp70 deliver preproteins to the mitochondrial import receptor Tom70," *Cell*, 112:41-50, 2003.

Zhang et al., "Nucleic acid aptamers in human viral disease," *Arch. Immunol. Ther. Exp.*, 52:307-315, 2004.

Extended European Search Report, issued in European Patent Application No. EP 06802154.2, dated Feb. 10, 2010.

Shiraga et al., "MZF-1 and DbpA interact with Dnase I hypersensitive sites that correlate with expression of the human MUC1 mucin gene," *Experimental Cell Research*, 308:41-52, 2005.

* cited by examiner

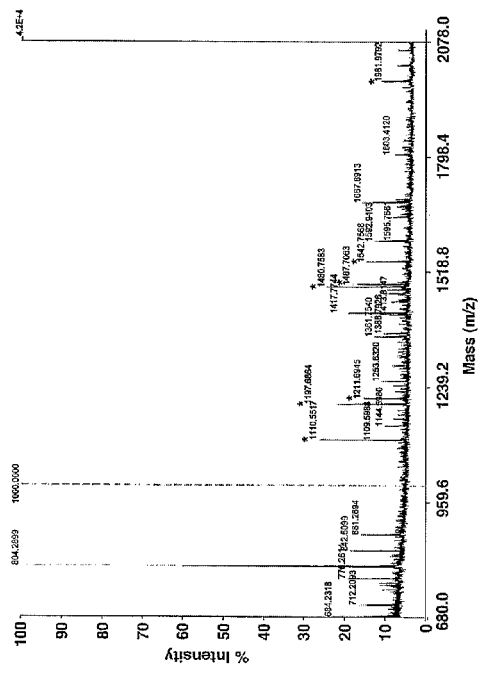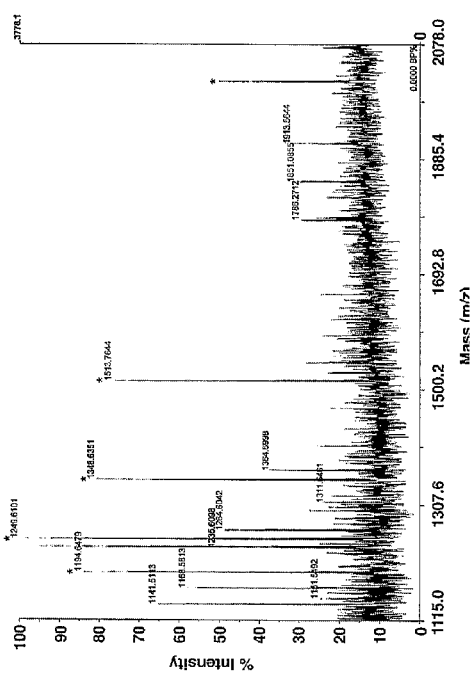
Fig. 1C  HSP70
Fig. 1D  HSP90

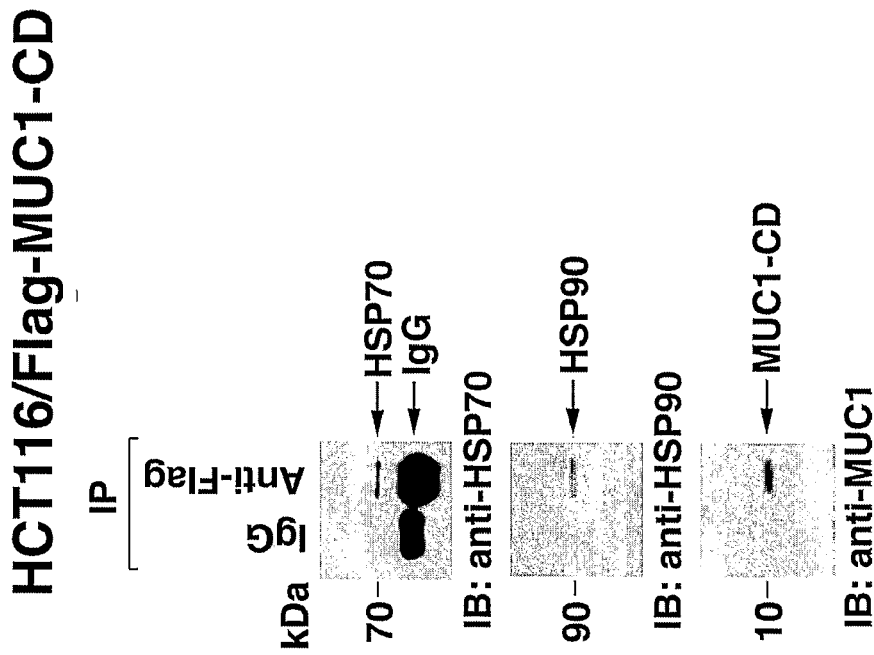
Fig. 2A HCT116/MUC1
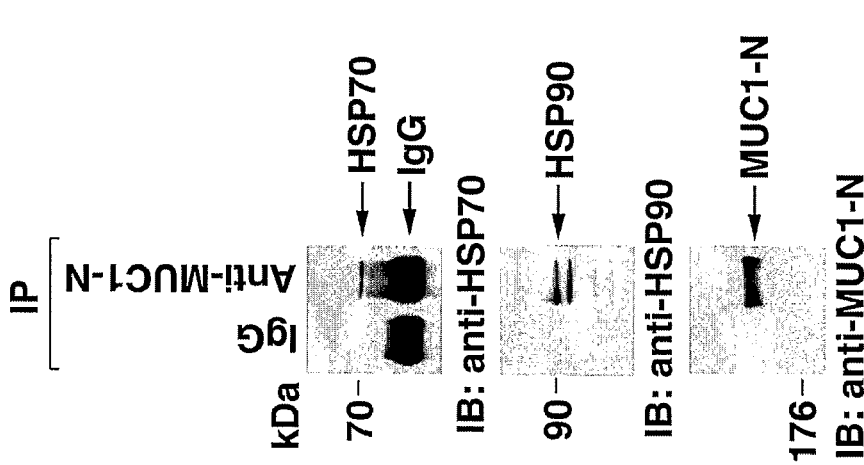
Fig. 2B HCT116/Flag-MUC1-CD

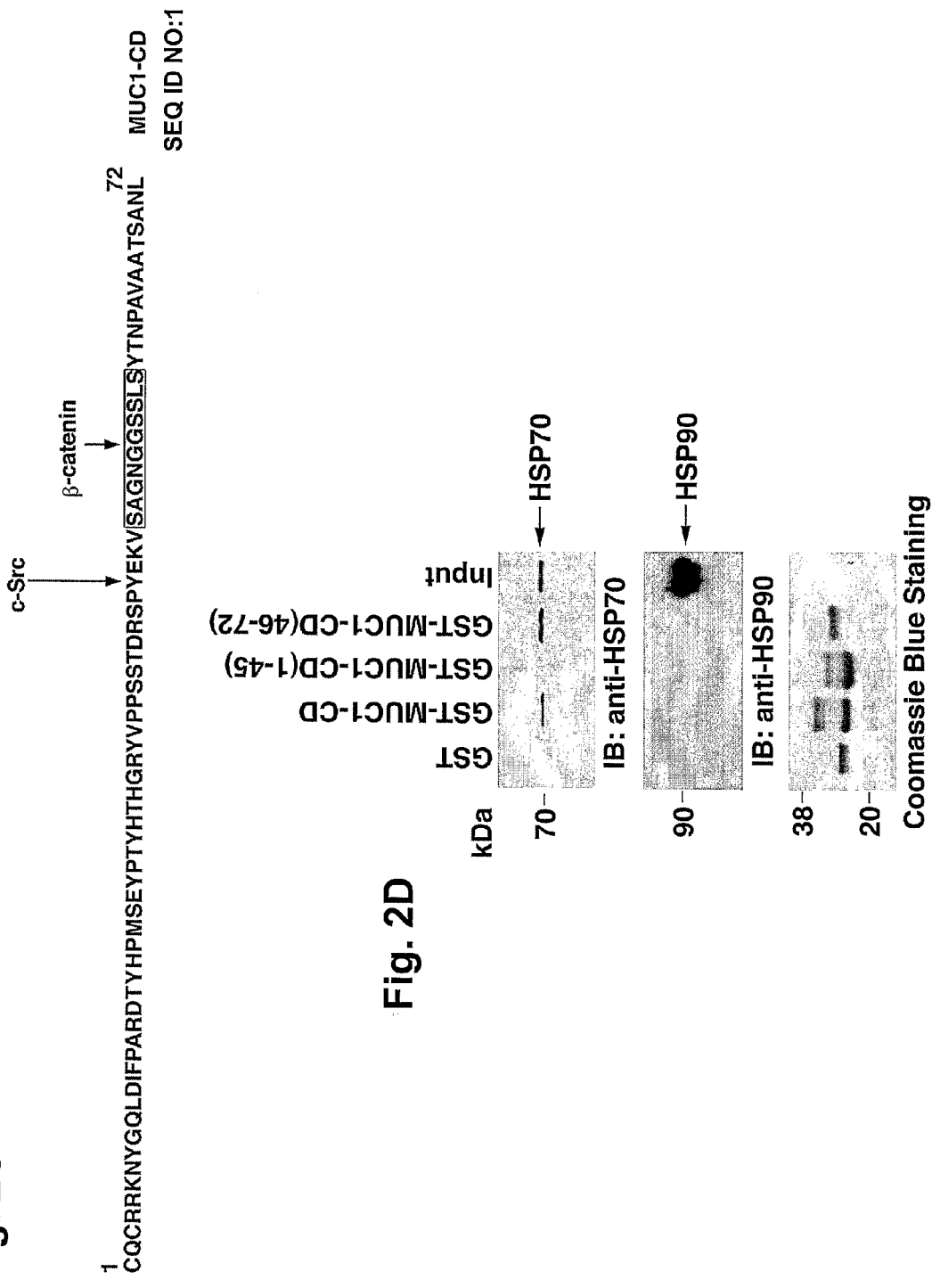

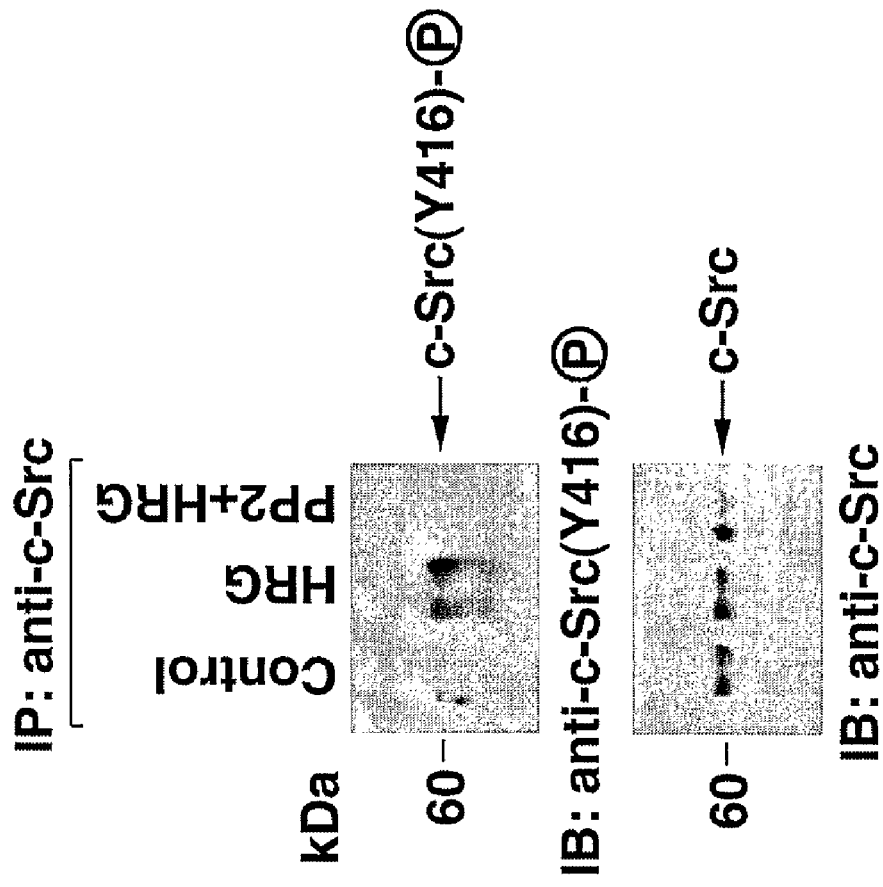

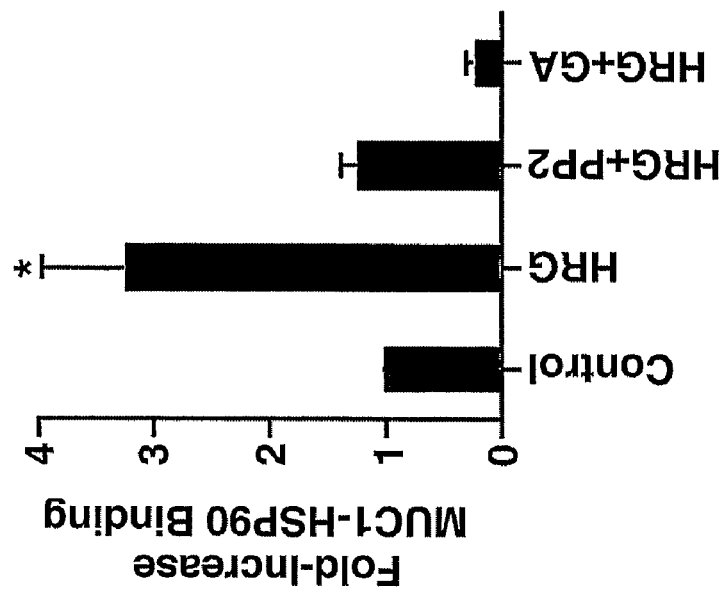
Fig. 3E
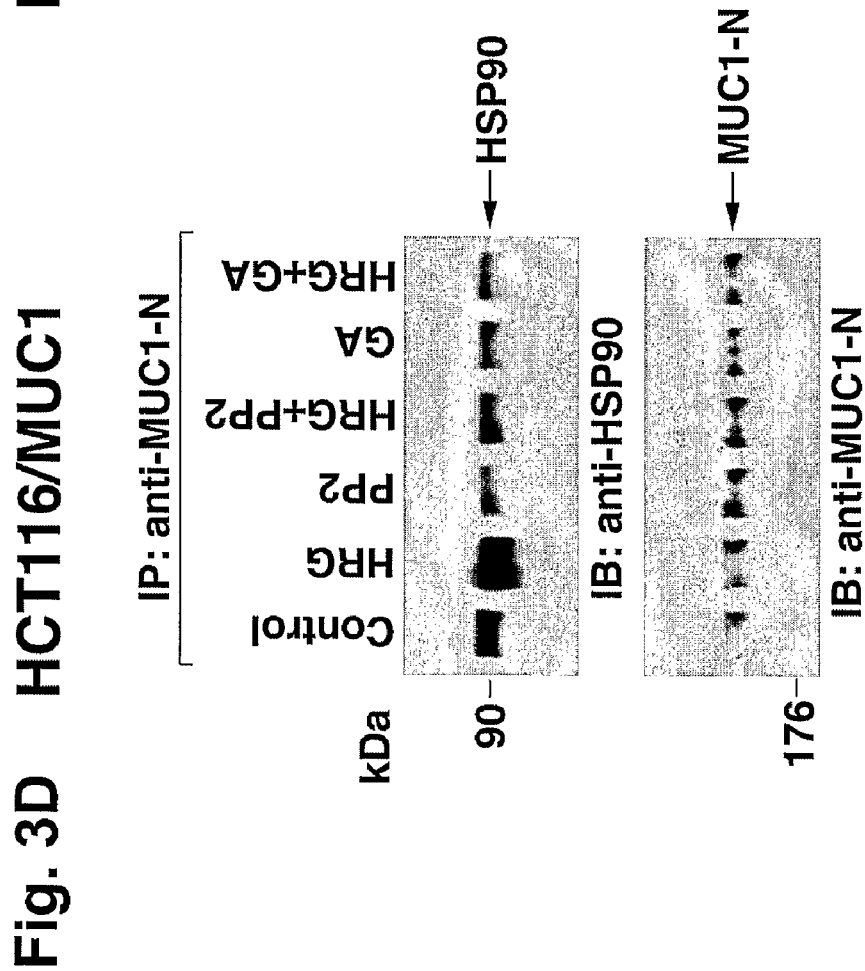
Fig. 3D  HCT116/MUC1

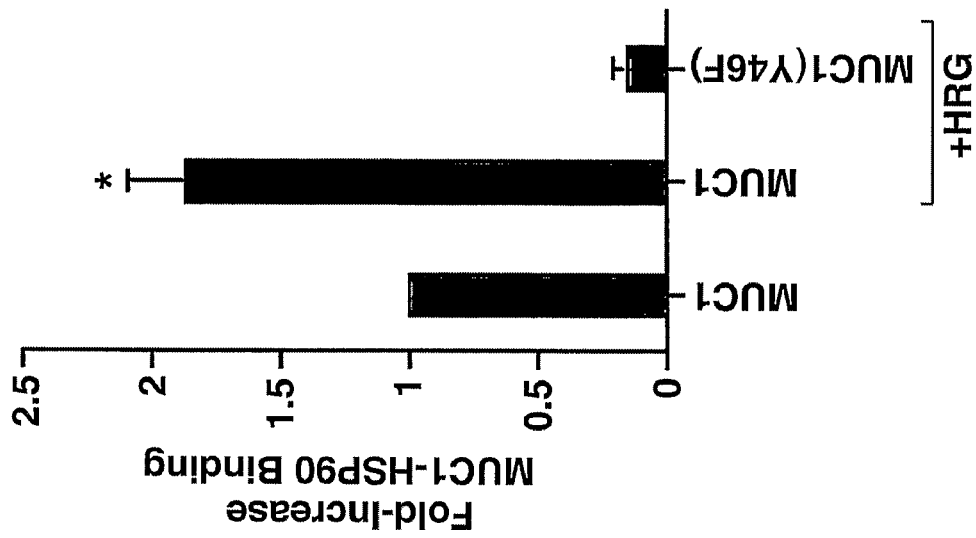
Fig. 3G
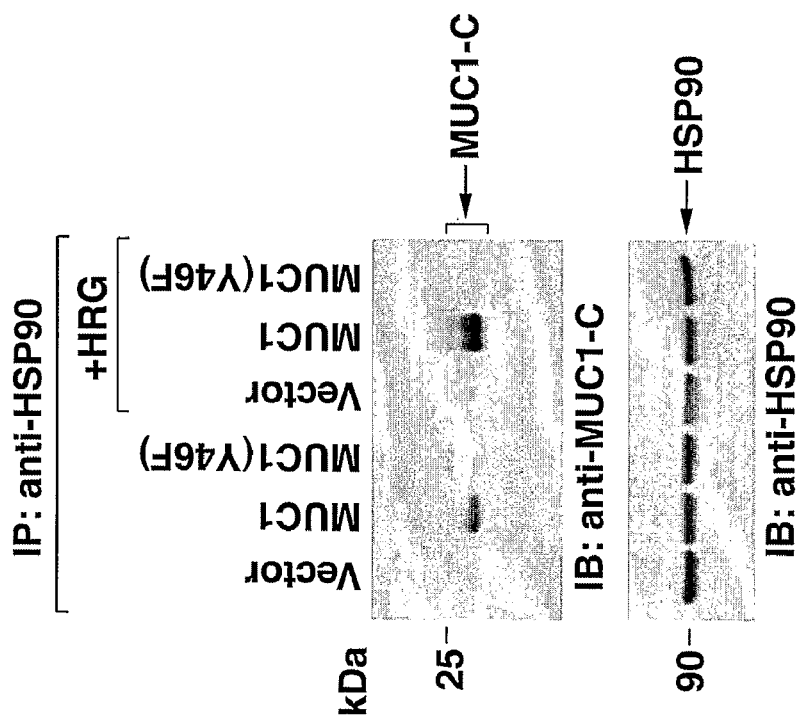
Fig. 3F  HCT116

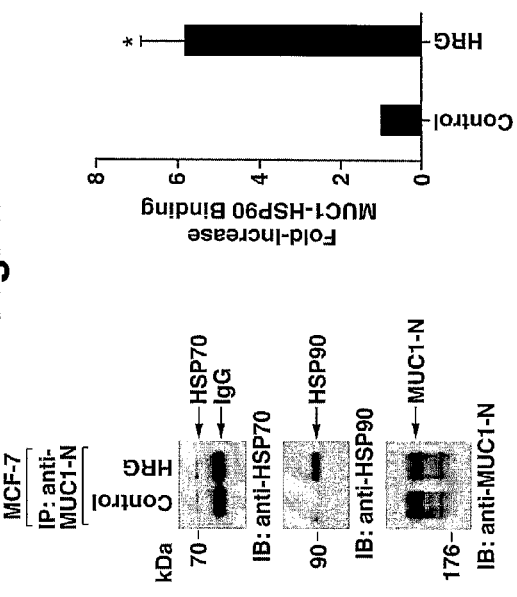
Fig. 4A
Fig. 4B
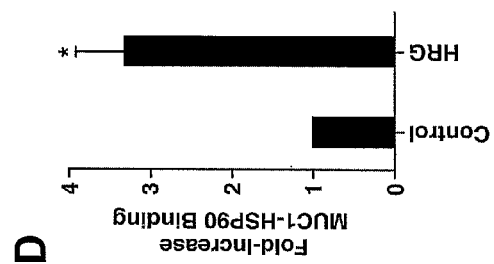
Fig. 4C
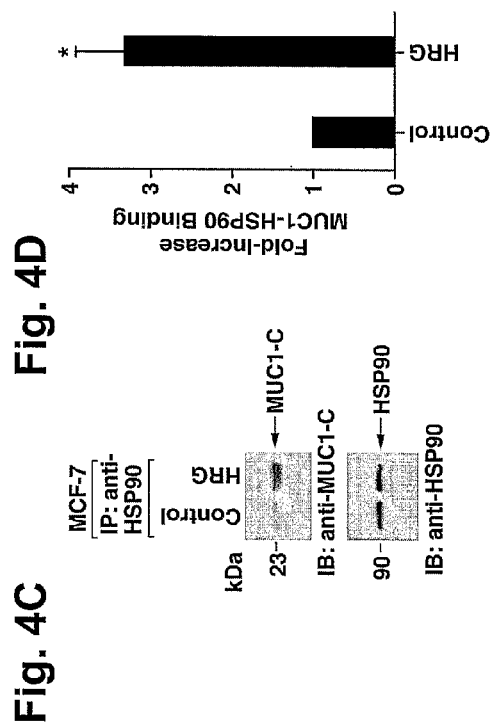
Fig. 4D

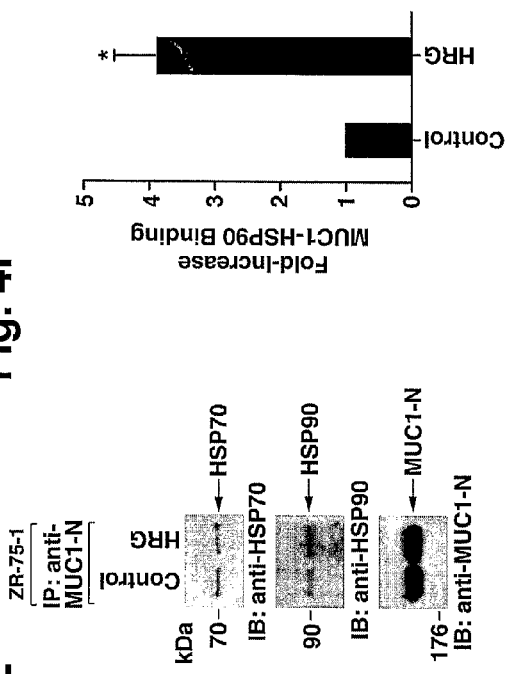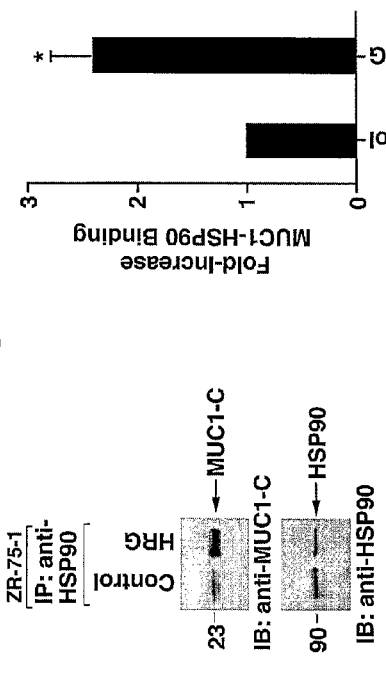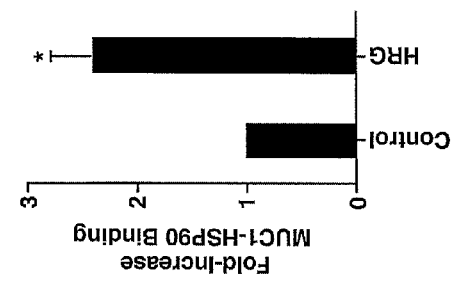

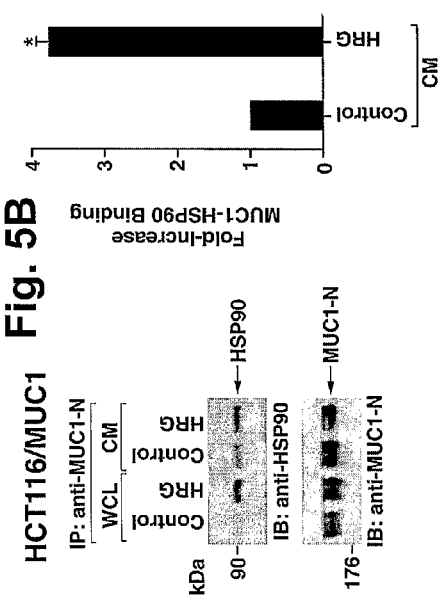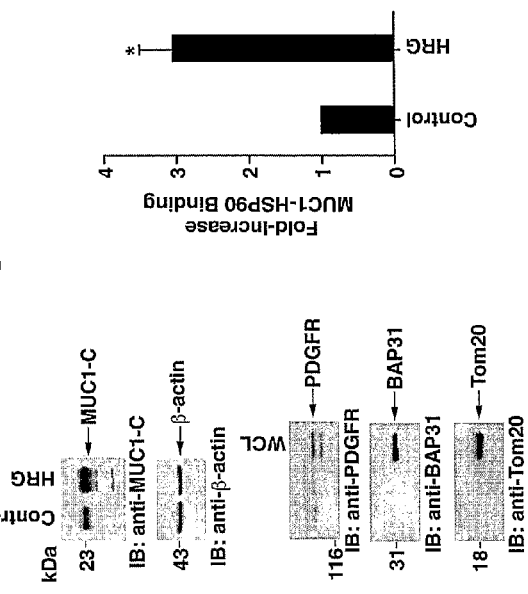

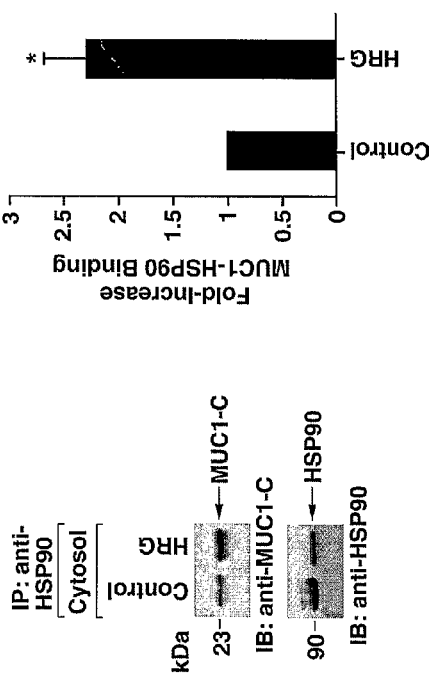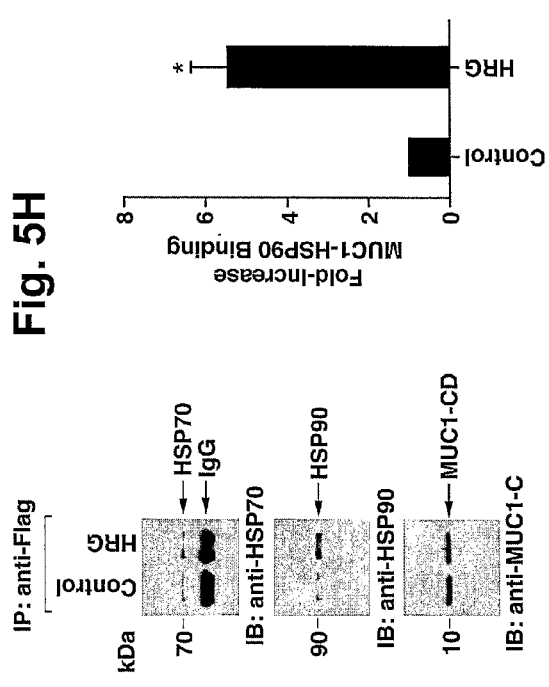

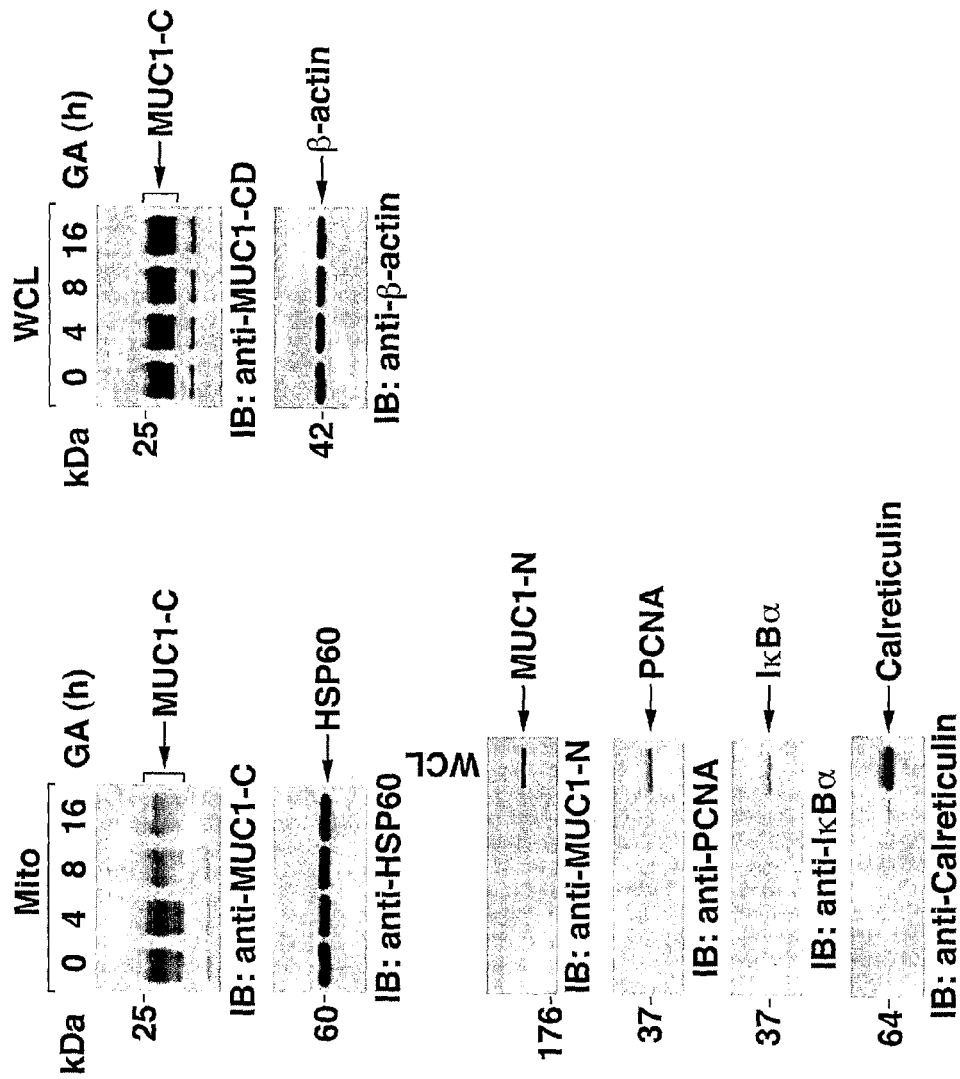
Fig. 6C HCT116/MUC1

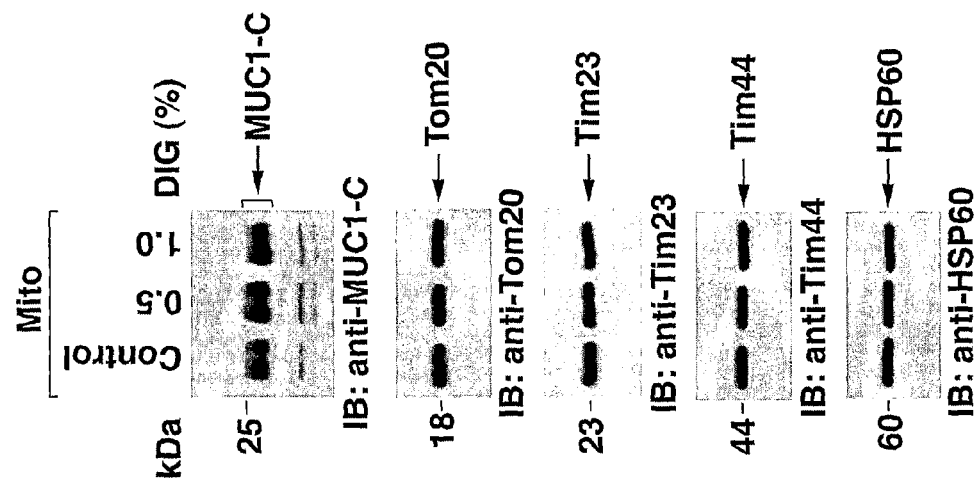
Fig. 7A
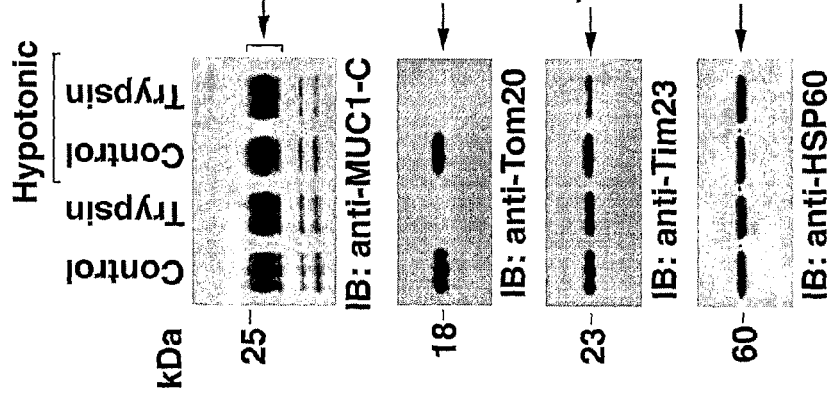
Fig. 7B  HCT116/MUC1

SEQUENCE LISTING

<160> NUMBER OF SEQ ID NOS: 5

<210> SEQ ID NO 1
<211> LENGTH: 72
<212> TYPE: PRT
<213> ORGANISM: Homo sapiens

<400> SEQUENCE: 1

```
Cys Gln Cys Arg Arg Lys Asn Tyr Gly Gln Leu Asp Ile Phe Pro Ala
1               5                   10                  15

Arg Asp Thr Tyr His Pro Met Ser Glu Tyr Pro Thr Tyr His Thr His
            20                  25                  30

Gly Arg Tyr Val Pro Pro Ser Ser Thr Asp Arg Ser Pro Tyr Glu Lys
        35                  40                  45

Val Ser Ala Gly Asn Gly Gly Ser Ser Leu Ser Tyr Thr Asn Pro Ala
    50                  55                  60

Val Ala Ala Thr Ser Ala Asn Leu
65                  70
```

<210> SEQ ID NO 2
<211> LENGTH: 26
<212> TYPE: PRT
<213> ORGANISM: Homo sapiens

<400> SEQUENCE: 2

```
Tyr Glu Lys Val Ser Ala Gly Asn Gly Gly Ser Ser Leu Ser Tyr Thr
1               5                   10                  15

Asn Pro Ala Val Ala Ala Thr Ser Ala Asn
            20                  25
```

<210> SEQ ID NO 3
<211> LENGTH: 701
<212> TYPE: PRT
<213> ORGANISM: Homo sapiens

<400> SEQUENCE: 3

```
Met Ser Val Val Gly Ile Asp Leu Gly Phe Gln Ser Cys Tyr Val Ala
1               5                   10                  15

Val Ala Arg Ala Gly Gly Ile Glu Thr Ile Ala Asn Glu Tyr Ser Asp
            20                  25                  30

Arg Cys Thr Pro Ala Cys Ile Ser Phe Gly Pro Lys Asn Arg Ser Ile
        35                  40                  45

Gly Ala Ala Ala Lys Ser Gln Val Ile Ser Asn Ala Lys Asn Thr Val
    50                  55                  60

Gln Gly Phe Lys Arg Phe His Gly Arg Ala Phe Ser Asp Pro Phe Val
65                  70                  75                  80
```

```
Glu Ala Glu Lys Ser Asn Leu Ala Tyr Asp Ile Val Gln Trp Pro Thr
                85                  90                  95
Gly Leu Thr Gly Ile Lys Val Thr Tyr Met Glu Glu Arg Asn Phe
            100                 105                 110
Thr Thr Glu Gln Val Thr Ala Met Leu Leu Ser Lys Leu Lys Glu Thr
                115                 120                 125
Ala Glu Ser Val Leu Lys Lys Pro Val Asp Cys Val Val Ser Val
    130                 135                 140
Pro Cys Phe Tyr Thr Asp Ala Glu Arg Arg Ser Val Met Asp Ala Thr
145                 150                 155                 160
Gln Ile Ala Gly Leu Asn Cys Leu Arg Leu Met Asn Glu Thr Thr Ala
                165                 170                 175
Val Ala Leu Ala Tyr Gly Ile Tyr Lys Gln Asp Leu Pro Arg Leu Glu
                180                 185                 190
Glu Lys Pro Arg Asn Val Val Phe Val Asp Met Gly His Ser Ala Tyr
            195                 200                 205
Gln Val Ser Val Cys Ala Phe Asn Arg Gly Lys Leu Lys Val Leu Ala
    210                 215                 220
Thr Ala Phe Asp Thr Thr Leu Gly Gly Arg Lys Phe Asp Glu Val Leu
225                 230                 235                 240
Val Asn His Phe Cys Glu Glu Phe Gly Lys Lys Tyr Lys Leu Asp Ile
                245                 250                 255
Lys Ser Lys Ile Arg Ala Leu Leu Arg Leu Ser Gln Glu Cys Glu Lys
            260                 265                 270
Leu Lys Lys Leu Met Ser Ala Asn Ala Ser Asp Leu Pro Leu Ser Ile
    275                 280                 285
Glu Cys Phe Met Asn Asp Val Asp Val Ser Gly Thr Met Asn Arg Gly
290                 295                 300
Lys Phe Leu Glu Met Cys Asn Asp Leu Leu Ala Arg Val Glu Pro Pro
305                 310                 315                 320
Leu Arg Ser Val Leu Glu Gln Thr Lys Leu Lys Lys Glu Asp Ile Tyr
                325                 330                 335
Ala Val Glu Ile Val Gly Gly Ala Thr Arg Ile Pro Ala Val Lys Glu
            340                 345                 350
Lys Ile Ser Lys Phe Phe Gly Lys Glu Leu Ser Thr Thr Leu Asn Ala
    355                 360                 365
Asp Glu Ala Val Thr Arg Gly Cys Ala Leu Gln Cys Ala Ile Leu Ser
370                 375                 380
Pro Ala Phe Lys Val Arg Glu Phe Ser Ile Thr Asp Val Val Pro Tyr
385                 390                 395                 400
Pro Ile Ser Leu Arg Trp Asn Ser Pro Ala Glu Glu Gly Ser Ser Asp
                405                 410                 415
Cys Glu Val Phe Ser Lys Asn His Ala Ala Pro Phe Ser Lys Val Leu
            420                 425                 430
Thr Phe Tyr Arg Lys Glu Pro Phe Thr Leu Glu Ala Tyr Tyr Ser Ser
    435                 440                 445
Pro Gln Asp Leu Pro Tyr Pro Asp Pro Ala Ile Ala Gln Phe Ser Val
450                 455                 460
Gln Lys Val Thr Pro Gln Ser Asp Gly Ser Ser Ser Lys Val Lys Val
465                 470                 475                 480
Lys Val Arg Val Asn Val His Gly Ile Phe Ser Val Ser Ser Ala Ser
                485                 490                 495
Leu Val Glu Val His Lys Ser Glu Glu Asn Glu Glu Pro Met Glu Thr
```

```
                    500             505             510
Asp Gln Asn Ala Lys Glu Glu Lys Met Gln Val Asp Gln Glu Glu
            515             520             525

Pro His Val Glu Glu Gln Gln Gln Thr Pro Ala Glu Asn Lys Ala
            530             535             540

Glu Ser Glu Glu Met Glu Thr Ser Gln Ala Gly Ser Lys Asp Lys Lys
545                 550             555                 560

Met Asp Gln Pro Pro Gln Cys Gln Glu Gly Lys Ser Glu Asp Gln Tyr
                565             570             575

Cys Gly Pro Ala Asn Arg Glu Ser Ala Ile Trp Gln Ile Asp Arg Glu
            580             585             590

Met Leu Asn Leu Tyr Ile Glu Asn Glu Gly Lys Met Ile Met Gln Asp
            595             600             605

Lys Leu Glu Lys Glu Arg Asn Asp Ala Lys Asn Ala Val Glu Glu Tyr
            610             615             620

Val Tyr Glu Met Arg Asp Lys Leu Ser Gly Glu Tyr Glu Lys Phe Val
625             630             635             640

Ser Glu Asp Asp Arg Asn Ser Phe Thr Leu Lys Leu Glu Asp Thr Glu
                645             650             655

Asn Trp Leu Tyr Glu Asp Gly Glu Asp Gln Pro Lys Gln Val Tyr Val
            660             665             670

Asp Lys Leu Ala Glu Leu Lys Asn Leu Gly Gln Pro Ile Lys Ile Arg
            675             680             685

Phe Gln Glu Ser Glu Glu Arg Pro Asn Tyr Leu Lys Asn
            690             695             700

<210> SEQ ID NO 4
<211> LENGTH: 724
<212> TYPE: PRT
<213> ORGANISM: Homo sapiens

<400> SEQUENCE: 4

Met Pro Glu Glu Val His His Gly Glu Glu Val Glu Thr Phe Ala
1               5               10              15

Phe Gln Ala Glu Ile Ala Gln Leu Met Ser Leu Ile Ile Asn Thr Phe
            20              25              30

Tyr Ser Asn Lys Glu Ile Phe Leu Arg Glu Leu Ile Ser Asn Ala Ser
            35              40              45

Asp Ala Leu Asp Lys Ile Arg Tyr Glu Ser Leu Thr Asp Pro Ser Lys
            50              55              60

Leu Asp Ser Gly Lys Glu Leu Lys Ile Asp Ile Ile Pro Asn Pro Gln
65              70              75              80

Glu Arg Thr Leu Thr Leu Val Asp Thr Gly Ile Gly Met Thr Lys Ala
            85              90              95

Asp Leu Ile Asn Asn Leu Gly Thr Ile Ala Lys Ser Gly Thr Lys Ala
            100             105             110

Phe Met Glu Ala Leu Gln Ala Gly Ala Asp Ile Ser Met Ile Gly Gln
            115             120             125

Phe Gly Val Gly Phe Tyr Ser Ala Tyr Leu Val Ala Glu Lys Val Val
            130             135             140

Val Ile Arg Lys His Asn Asp Asp Glu Gln Tyr Ala Trp Glu Ser Ser
145             150             155             160

Ala Gly Gly Ser Phe Thr Val Arg Ala Asp His Gly Glu Pro Ile Gly
            165             170             175

Met Gly Thr Lys Val Ile Leu His Leu Lys Glu Asp Gln Thr Glu Tyr
```

```
                180                 185                 190
Leu Glu Glu Arg Arg Val Lys Glu Val Val Lys Lys His Ser Gln Phe
            195                 200                 205

Ile Gly Tyr Pro Ile Thr Leu Tyr Leu Glu Lys Glu Arg Glu Lys Glu
        210                 215                 220

Ile Ser Asp Asp Glu Ala Glu Glu Lys Gly Lys Glu Glu
225                 230                 235                 240

Asp Lys Asp Asp Glu Glu Lys Pro Lys Ile Glu Asp Val Gly Ser Asp
                245                 250                 255

Glu Glu Asp Asp Ser Gly Lys Asp Lys Lys Lys Thr Lys Lys Ile
            260                 265                 270

Lys Glu Lys Tyr Ile Asp Gln Glu Glu Leu Asn Lys Thr Lys Pro Ile
                275                 280                 285

Trp Thr Arg Asn Pro Asp Asp Ile Thr Gln Glu Glu Tyr Gly Glu Phe
        290                 295                 300

Tyr Lys Ser Leu Thr Asn Asp Trp Glu Asp His Leu Ala Val Lys His
305                 310                 315                 320

Phe Ser Val Glu Gly Gln Leu Glu Phe Arg Ala Leu Leu Phe Ile Pro
                325                 330                 335

Arg Arg Ala Pro Phe Asp Leu Phe Glu Asn Lys Lys Lys Asn Asn
        340                 345                 350

Ile Lys Leu Tyr Val Arg Arg Val Phe Ile Met Asp Ser Cys Asp Glu
            355                 360                 365

Leu Ile Pro Glu Tyr Leu Asn Phe Ile Arg Gly Val Val Asp Ser Glu
        370                 375                 380

Asp Leu Pro Leu Asn Ile Ser Arg Glu Met Leu Gln Gln Ser Lys Ile
385                 390                 395                 400

Leu Lys Val Ile Arg Lys Asn Ile Val Lys Lys Cys Leu Glu Leu Phe
                405                 410                 415

Ser Glu Leu Ala Glu Asp Lys Glu Asn Tyr Lys Lys Phe Tyr Glu Ala
            420                 425                 430

Phe Ser Lys Asn Leu Lys Leu Gly Ile His Glu Asp Ser Thr Asn Arg
        435                 440                 445

Arg Arg Leu Ser Glu Leu Leu Arg Tyr His Thr Ser Gln Ser Gly Asp
    450                 455                 460

Glu Met Thr Ser Leu Ser Glu Tyr Val Ser Arg Met Lys Glu Thr Gln
465                 470                 475                 480

Lys Ser Ile Tyr Tyr Ile Thr Gly Glu Ser Lys Glu Gln Val Ala Asn
                485                 490                 495

Ser Ala Phe Val Glu Arg Val Arg Lys Arg Gly Phe Glu Val Val Tyr
        500                 505                 510

Met Thr Glu Pro Ile Asp Glu Tyr Cys Val Gln Gln Leu Lys Glu Phe
    515                 520                 525

Asp Gly Lys Ser Leu Val Ser Val Thr Lys Glu Gly Leu Glu Leu Pro
        530                 535                 540

Glu Asp Glu Glu Glu Lys Lys Met Glu Glu Ser Lys Ala Lys Phe
545                 550                 555                 560

Glu Asn Leu Cys Lys Leu Met Lys Glu Ile Leu Asp Lys Lys Val Glu
                565                 570                 575

Lys Val Thr Ile Ser Asn Arg Leu Val Ser Ser Pro Cys Cys Ile Val
        580                 585                 590

Thr Ser Thr Tyr Gly Trp Thr Ala Asn Met Glu Arg Ile Met Lys Ala
    595                 600                 605
```

```
Gln Ala Leu Arg Asp Asn Ser Thr Met Gly Tyr Met Met Ala Lys Lys
            610                 615                 620

His Leu Glu Ile Asn Pro Asp His Pro Ile Val Glu Thr Leu Arg Gln
625             630                 635                 640

Lys Ala Glu Ala Asp Lys Asn Asp Lys Ala Val Lys Asp Leu Val Val
                645                 650                 655

Leu Leu Phe Glu Thr Ala Leu Leu Ser Ser Gly Phe Ser Leu Glu Asp
                660                 665                 670

Pro Gln Thr His Ser Asn Arg Ile Tyr Arg Met Ile Lys Leu Gly Leu
            675                 680                 685

Gly Ile Asp Glu Asp Glu Val Ala Ala Glu Glu Pro Asn Ala Ala Val
            690                 695                 700

Pro Asp Glu Ile Pro Pro Leu Glu Gly Asp Glu Asp Ala Ser Arg Met
705             710                 715                 720

Glu Glu Val Asp

<210> SEQ ID NO 5
<211> LENGTH: 159
<212> TYPE: PRT
<213> ORGANISM: Homo sapiens

<400> SEQUENCE: 5

Gly Ser Val Val Val Gln Leu Thr Leu Ala Phe Arg Glu Gly Thr Ile
1               5                   10                  15

Asn Val His Asp Val Glu Thr Gln Phe Asn Gln Tyr Lys Thr Glu Ala
                20                  25                  30

Ala Ser Arg Tyr Asn Leu Thr Ile Ser Asp Val Ser Val Ser Asp Val
            35                  40                  45

Pro Phe Pro Phe Ser Ala Gln Ser Gly Ala Gly Val Pro Gly Trp Gly
        50                  55                  60

Ile Ala Leu Leu Val Leu Val Cys Val Leu Val Ala Leu Ala Ile Val
65                  70                  75                  80

Tyr Leu Ile Ala Leu Ala Val Cys Gln Cys Arg Arg Lys Asn Tyr Gly
                85                  90                  95

Gln Leu Asp Ile Phe Pro Ala Arg Asp Thr Tyr His Pro Met Ser Glu
            100                 105                 110

Tyr Pro Thr Tyr His Thr His Gly Arg Tyr Val Pro Pro Ser Ser Thr
        115                 120                 125

Asp Arg Ser Pro Tyr Glu Lys Val Ser Ala Gly Asn Gly Gly Ser Ser
    130                 135                 140

Leu Ser Tyr Thr Asn Pro Ala Val Ala Ala Thr Ser Ala Asn Leu
145                 150                 155
```

MITOCHONDRIAL LOCALIZATION OF MUC1

RELATED APPLICATIONS

This patent application is a national phase application under 35 U.S.C. §371 of International Application No. PCT/US2006/032906 filed Aug. 21, 2006, which claims priority to U.S. provisional application Ser. No. 60/710,166, filed Aug. 22, 2005, the entire contents of which are hereby incorporated by reference.

SEQUENCE LISTING

The entire content of the electronic submission of the sequence listing filed via the USPTO EFS-WEB server Feb. 23, 2011 is incorporated herein by reference in its entirety. The sequence listing is identified on the electronically filed text file as follows:
File Name: GENU:020.txt
Date of Creation: Jan. 28, 2010
Size (bytes): 14,600.

TECHNICAL FIELD

This invention relates to regulation of cell growth, and more particularly to regulation of cancer cell growth.

BACKGROUND

The MUC1 protein is overexpressed by greater than 800,000 of the 1.3 million tumors diagnosed in the United States each year.

SUMMARY

The inventors have found that MUC1 binds to the HSP70 and HSP90 chaperones and that this binding is important for targeting of MUC1 to the mitochondria, where it attenuates stress-induced apoptosis. MUC1 binds to HSP70 and HSP90 independently, and c-Src is involved in MUC1-HSP90 binding. The invention includes methods for identifying compounds useful for inhibiting the interaction between MUC1 and HSP70 or HSP90. Such compounds can be useful for directly promoting apoptosis of MUC1-expressing cancer cells, for enhancing the efficacy of genotoxic chemotherapeutic agents against such cancer cells, and as anti-cancer prophylactic agents. Also included in the invention are methods of inhibiting the interaction between HSP70 or HSP90 and MUC1 in which cells (e.g., carcinoma cells such as breast carcinoma cells) are contacted with compounds that inhibit the interaction between MUC1 and HSP70 or HSP90. While the experiments described herein were generally performed with human MUC1, MUC1-binders, and cells, it is understood that the methods described herein can be performed with corresponding molecules from any of the mammalian species recited below.

The invention includes methods of identifying compounds that inhibit binding of MUC1 to HSP70. The methods include: (a) providing a MUC1 test agent; (b) providing a HSP70 test agent that binds to the MUC1 test agent; (c) contacting the MUC1 test agent with the HSP70 test agent in the presence of a test compound under conditions that permit the binding of the MUC1 test agent with the HSP70 test agent in absence of the test compound; and (d) determining whether the test compound inhibits binding of the MUC1 test agent to the HSP70 test agent. The contacting can be carried out in a cell-free system or it can occur in a cell.

The invention also includes methods of identifying compounds that inhibit binding of MUC1 to HSP90. The methods include: (a) providing a MUC1 test agent, e.g., a phosphorylated MUC1 test agent; (b) providing a HSP90 test agent that binds to the MUC1 test agent; (c) contacting the MUC1 test agent with the HSP90 test agent in the presence of a test compound under conditions that permit the binding of the MUC1 test agent with the HSP70 test agent in absence of the test compound; and (d) determining whether the test compound inhibits binding of the MUC1 test agent to the HSP90 test agent. The contacting can be carried out in a cell-free system or it can occur in a cell. The HSP90 test agent is phosphorylated by c-Src. In some embodiments, the contacting is performed in the presence of c-Src.

Also featured by the invention are methods of generating compounds that inhibit the interaction between MUC1 and HSP70 of HSP90. The methods include: (a) providing the three-dimensional structure of a molecule containing the cytoplasmic domain of MUC1 or HSP70 or HSP90 (e.g., the substrate binding domain of HSP70 or HSP90); (b) designing, based on the three dimensional structure, a compound containing a region that inhibits the interaction between MUC1 and HSP70 or the interaction between MUC1 and HSP90; and (c) producing the compound.

Another embodiment of the invention is a process of manufacturing a compound. The process includes: (a) performing the method described in the previous paragraph; and (b) after determining that the compound inhibits the interaction between MUC1 and HSP70 or MUC1 and HSP90, manufacturing the compound.

In another aspect, the invention provides in vivo methods of inhibiting binding of MUC1 to HSP70 or HSP90 in a cancer cell that expresses MUC1. The methods include: (a) identifying a subject as having a cancer that expresses MUC1 or is suspected to express MUC1; and (b) administering to the subject a compound or, where the compound is a polypeptide, a nucleic acid containing a nucleic acid sequence encoding the polypeptide, the nucleic acid sequence being operably linked to a transcriptional regulatory element (TRE), wherein the compound inhibits binding of HSP70 or HSP90 to the cytoplasmic domain of MUC1. The compound can be a peptide fragment of (a) MUC1, (b) HSP70, or (c) HSP90. Thus, the compound can be a peptide fragment of the cytoplasmic domain of MUC1. The compound can be a peptide fragment that includes all or part of amino acids 46-72 of SEQ ID NO:1. It can be or include all or part of the substrate binding domain of HSP70 or HSP90. Moreover, the compound can be an antibody, or an antibody fragment, that binds to the cytoplasmic domain of MUC1. Alternatively, the compound can be a small molecule, e.g., a small molecule that is or contains a nucleic acid aptamer. The subject can be a human subject. The cancer cell can be, e.g., a breast cancer, lung cancer, colon cancer, pancreatic cancer, renal cancer, stomach cancer, liver cancer, bone cancer, hematological cancer, neural tissue cancer, melanoma, ovarian cancer, testicular cancer, prostate cancer, cervical cancer, vaginal cancer, or bladder cancer cell. The TRE can be a DF3 enhancer.

Also embraced by the invention are methods of killing a cancer cell. The methods can include, before, after, or at the same time as performing the methods described in the previous paragraph, exposing the subject to one or more genotoxic agents. The genotoxic agents can be, for example, one or more forms of ionizing radiation and/or one or more chemotherapeutic agents. The one or more chemotherapeutic agents can be, for example, cisplatin, carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide, verampil, podophyllotoxin, tamoxifen, taxol, transplatinum, 5-fluorouracil, vincristin, vinblastin, methotrexate, or an analog of any of the aforementioned.

"Polypeptide" and "protein" are used interchangeably and mean any peptide-linked chain of amino acids, regardless of length or post-translational modification. The MUC1 and MUC1-binder molecules and test agents used in any of the methods of the invention can contain or be wild-type proteins or can be variants that have one or more (e.g., one, two, three, four, five, six, seven, eight, nine, ten, 12, 15, 20, 25, 30, 35, 40, or 50) conservative amino acid substitutions. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. All that is required is that: (i) such variants of MUC1 have at least 25% (e.g., at least: 30%; 40%; 50%; 60%; 70%; 75%; 80%; 85%; 90%; 95%; 97%; 98%; 99%; 99.5%, or 100% or even greater) of the ability of wild-type MUC1-C to bind to HSP70 or HSP90; and (ii) such variants of a MUC1-binder have at least 25% (e.g., at least: 30%; 40%; 50%; 60%; 70%; 75%; 80%; 85%; 90%; 95%; 97%; 98%; 99%; 99.5%, or 100% or even greater) of the ability of the relevant wild-type MUC1-binder to bind to MUC1-C.

As used herein, a "MUC1-binder" is HSP70 or HSP90.

As used herein, a "MUC1-binder test agent" contains, or is, (a) the full-length, wild-type MUC1-binder, (b) a part of the MUC1-binder that is shorter than the full-length MUC1-binder, or (c) (a) or (b) but with one or more (see above) conservative substitutions. "Parts of a MUC1-binder" include fragments as well deletion variants (terminal as well internal deletions) of the MUC1-binder. Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. MUC1-binder test agents can include internal or terminal (C or N) irrelevant amino acid sequences (e.g., sequences derived from other proteins or synthetic sequences not corresponding to any naturally occurring protein). These added irrelevant sequences will generally be about 1 to 50 (e.g., two, four, eight, ten, 15, 20, 25, 30, 35, 40, or 45) amino acids in length. MUC1-binder test agents other than full-length wild-type MUC1-binder molecules will have at least 50% (e.g., at least 50%, at least 60%, at least 70%, at least 80%, at least 90%, at least 95%, at least 98%, at least 99%, at least 99.5%, or 100% or more) of the ability of the full-length wild-type MUC1-binder to bind to the cytoplasmic domain of MUC1.

As used herein, a "MUC1 test agent" contains, or is, (a) full-length, wild-type mature MUC1, (b) a part of MUC1 that is shorter than full-length, wild-type, mature MUC1, or (c) (a) or (b) but with one or more (see above) conservative substitutions. "Parts of a MUC1" include fragments (e.g., MUC1-C or the cytoplasmic domain (CD) of MUC1) as well as deletion variants (terminal as well internal deletions) of MUC1. Deletion variants can lack one, two, three, four, five, six, seven, eight, nine, ten, 11, 12, 13, 14, 15, 16, 17, 18, 19, or 20 amino acid segments (of two or more amino acids) or non-contiguous single amino acids. MUC1 test agents can include internal or terminal (carboxy or amino) irrelevant amino acid sequences (e.g., sequences derived from other proteins or synthetic sequences not corresponding to any naturally occurring protein). These added irrelevant sequences will generally be about 1 to 50 (e.g., two, four, eight, ten, 15, 20, 25, 30, 35, 40, or 45) amino acids in length. MUC1 test agents other than full-length, wild-type, mature MUC1 will have at least 50% (e.g., at least 50%, at least 60%, at least 70%, at least 80%, at least 90%, at least 95%, at least 98%, at least 99%, at least 99.5%, or 100% or more) of the ability of the full-length, wild-type, mature MUC1-binder to bind to HSP70 or HSP90. Both MUC1 test agents and parts of a MUC1 can be phosphorylated, e.g., on a tyrosine residue.

As used herein, "operably linked" means incorporated into a genetic construct so that expression control sequences effectively control expression of a coding sequence of interest.

Unless otherwise defined, all technical and scientific terms used herein have the same meaning as commonly understood by one of ordinary skill in the art to which this invention pertains. In case of conflict, the present document, including definitions, will control. Preferred methods and materials are described below, although methods and materials similar or equivalent to those described herein can also be used in the practice or testing of the present invention. All publications, patent applications, patents and other references mentioned herein are incorporated by reference in their entirety. The materials, methods, and examples disclosed herein are illustrative only and not intended to be limiting.

Other features and advantages of the invention, e.g., inhibiting survival of cancer cells, will be apparent from the following description, from the drawings and from the claims.

DESCRIPTION OF DRAWINGS

FIGS. 1C and 1D are MALDI-TOF-MS spectra of 70 and 90 kDa immunoprecipitated proteins. FIG. 1C depicts the analysis of the 70 kDa protein with peptides corresponding to HSP70 shown with an asterisk. FIG. 1D depicts the analysis of the 90 kDa protein with peptides corresponding to HSP90 shown with an asterisk.

FIGS. 2A and 2B are series of immunoblots of immunoprecipitated lysates. FIG. 2A depicts immunoblots of lysates from HCT116/MUC1 cells subjected to immunoprecipitation with anti-MUC1-N or a control mouse IgG. The precipitates were analyzed by immunoblotting with the indicated antibodies (anti-HSP70, anti-HSP90, or anti-MUC1-N). FIG. 2B depicts immunoblots of immunoprecipitated lysates from HCT116 cells stably expressing Flag-MUC1-CD subjected to immunoprecipitation with anti-MUC1-N or a control mouse IgG. The precipitates were analyzed by immunoblotting with the indicated antibodies (anti-HSP70, anti-HSP90, or anti-MUC1-N).

FIG. 2C depicts the amino acid sequence of MUC1-CD (SEQ ID NO:1). The c-Src phosphorylation site at Y-46 and the β-catenin binding domain are highlighted.

FIG. 2D is a series of immunoblots of adsorbates of recombinant HSP70 or HSP 90 incubated with GST, GST-MUC1-CD, GST-MUC1-CD(1-45) and GST-MUC1-CD(46-72) bound to glutathione beads. The adsorbates were immunoblotted with the indicated antibodies (HSP70 and HSP90). Input lanes show total amounts of HSP70 and HSP90 proteins added to the reactions. Loading of the GST proteins was assessed by Coomassie blue staining.

FIG. 3C is a series of immunoblots of HCT116/MUC1 cell lysates immunoprecipitated with anti-c-Src. The cells were untreated prior to lysis or treated with 20 ng/ml HRG for 10 minutes or with 10 mM PP2 for 1 hour and then HRG.

FIG. 3D is a series of immunoblots of HCT116/MUC1 cell lysates immunoprecipitated with anti-MUC1-N. The cells were untreated prior to lysis or treated with 20 ng/ml HRG for 10 minutes or with 10 mM PP2 or 1 mM GA for 1 hour and then HRG. Anti-MUC1-N immunoprecipitates were immunoblotted with the indicated antibodies.

FIG. 3E is a bar graph depicting the intensities of the signals in FIG. 3D as assessed by densitometric scanning. The fold-increase in MUC1-HSP90 binding is expressed as the mean±SEM of three separate experiments compared to that obtained with the MUC1 control (assigned a value of 1). The asterisk denotes $p<0.05$ as compared to control.

FIG. 3F is a series of immunoblots of anti-HSP90 immunoprecipitates of lysates of HCT116/vector, HCT116/MUC1 and HCT116/MUC1(Y46F) cells that were untreated or treated with HRG for 10 minutes. Anti-HSP90 immunoprecipitates were immunoblotted with the indicated antibodies.

FIG. 3G is a bar graph depicting the intensities of the signals in FIG. 3F as assessed by densitometric scanning. The fold-increase in MUC1-HSP90 binding is expressed as the mean±SEM of three separate experiments compared to that obtained with the MUC1 control (assigned a value of 1). The asterisk denotes $p<0.05$ as compared to control.

FIG. 4A is a series of immunoblots of lysates of MCF-7 cells immunoprecipitated with anti-MUC1-N. Cells were untreated or treated with HRG for 10 minutes. Anti-MUC1-N immunoprecipitates were immunoblotted with the indicated antibodies.

FIG. 4B is a bar graph depicting the intensities of the signals in FIG. 4A as assessed by densitometric scanning. The fold-increase in MUC1-HSP90 binding is expressed as the mean±SEM of three separate experiments compared to that obtained with the MUC1 control (assigned a value of 1). The asterisk denotes $p<0.05$ as compared to control.

FIG. 4C is a series of immunoblots of lysates of MCF-7 cells immunoprecipitated with anti-HSP-90. Cells were untreated or treated with HRG for 10 minutes. Anti-HSP-90 immunoprecipitates were immunoblotted with the indicated antibodies.

FIG. 4D is a bar graph depicting the intensities of the signals in FIG. 4C as assessed by densitometric scanning. The fold-increase in MUC1-HSP90 binding is expressed as the mean±SEM of three separate experiments compared to that obtained with the MUC1 control (assigned a value of 1). The asterisk denotes $p<0.05$ as compared to control.

FIG. 4E is a series of immunoblots of lysates of ZR-75-1 cells immunoprecipitated with anti-MUC1-N. Cells were untreated or treated with HRG for 10 minutes. Anti-MUC1-N immunoprecipitates were immunoblotted with the indicated antibodies.

FIG. 4F is a bar graph depicting the intensities of the signals in FIG. 4E as assessed by densitometric scanning. The fold-increase in MUC1-HSP90 binding is expressed as the mean±SEM of three separate experiments compared to that obtained with the MUC1 control (assigned a value of 1). The asterisk denotes $p<0.05$ as compared to control.

FIG. 4G is a series of immunoblots of lysates of ZR-75-1 cells immunoprecipitated with anti-HSP-90. Cells were untreated or treated with HRG for 10 minutes. Anti-HSP-90 immunoprecipitates were immunoblotted with the indicated antibodies.

FIG. 4H is a bar graph depicting the intensities of the signals in FIG. 4G as assessed by densitometric scanning. The fold-increase in MUC1-HSP90 binding is expressed as the mean±SEM of three separate experiments compared to that obtained with the MUC1 control (assigned a value of 1). The asterisk denotes $p<0.05$ as compared to control.

FIG. 5A is a series of immunoblots of whole cell lysates (WCL) and cell membrane (CM) preparations of HCT116/MUC1 cells immunoprecipitated with anti-MUC1-N. The cells were left untreated or stimulated with HRG for 10 minutes.

FIG. 5B is a bar graph depicting the intensities of the signals in FIG. 5A as assessed by densitometric scanning. The fold-increase in MUC1-HSP90 binding is expressed as the mean±SEM of three separate experiments compared to that obtained with the MUC1 control (assigned a value of 1). The asterisk denotes $p<0.05$ as compared to control.

FIG. 5C is a series of immunoblots of cytosolic fractions of HCT116/MUC1 cells immunoblotted with anti-MUC1-C and anti-β-actin. The cells were left untreated or stimulated with HRG for 10 minutes. The cytosolic fractions were also immunoblotted with antibodies against the cell membrane-associated PDGFR, ER-associated BAP31 and mitochondria-associated Tom20 proteins. Whole cell lysate (WCL) was included as a control.

FIG. 5D is a bar graph depicting the intensities of the signals in FIG. 5C as assessed by densitometric scanning. The fold-increase in MUC1-HSP90 binding is expressed as the mean±SEM of three separate experiments compared to that obtained with the MUC1 control (assigned a value of 1). The asterisk denotes $p<0.05$ as compared to control.

FIG. 5E is a series of immunoblots of anti-HSP90 precipitates from cytosolic fractions immunoblotted with anti-MUC1-C and anti-HSP90. The cells were left untreated or stimulated with HRG for 10 minutes.

FIG. 5F is a bar graph depicting the intensities of the signals in FIG. 5E as assessed by densitometric scanning. The fold-increase in MUC1-HSP90 binding is expressed as the mean±SEM of three separate experiments compared to that obtained with the MUC1 control (assigned a value of 1). The asterisk denotes $p<0.05$ as compared to control.

FIG. 5G is a series of immunoblots of anti-Flag precipitates from HCT116/Flag-MUC1-CD cells that were untreated or treated with HRG for 10 minutes. Anti-Flag precipitates were immunoblotted with the indicated antibodies.

FIG. 5H is a bar graph depicting the intensities of the signals in FIG. 5G as assessed by densitometric scanning. The fold-increase in MUC1-HSP90 binding is expressed as the mean±SEM of three separate experiments compared to that obtained with the MUC1 control (assigned a value of 1). The asterisk denotes $p<0.05$ as compared to control.

FIG. 6C is a series of immunoblots of mitochondrial or whole cell fractions of HCT116/MUC1 cells that were treated with 1 mM GA for the indicated times. Purified mitochondria (left) and whole cell lysates (right) were immunoblotted with the indicated antibodies.

FIG. 7A is a series of immunoblots of purified mitochondria from HCT116/MUC1 cells that were untreated or treated with 60 mg/ml trypsin for 15 minutes at 4° C. Mitochondria were also first incubated in hypotonic buffer before exposure to trypsin. Digestion of the proteins was analyzed by immunoblotting with the indicated antibodies.

FIG. 7B is a series of immunoblots of purified mitochondria from HCT116/MUC1 cells that were treated with 0.5% or 1.0% digitonin (DIG) for 15 minutes at 4° C. Lysates were immunoblotted with the indicated antibodies.

DETAILED DESCRIPTION

Figure 1A:
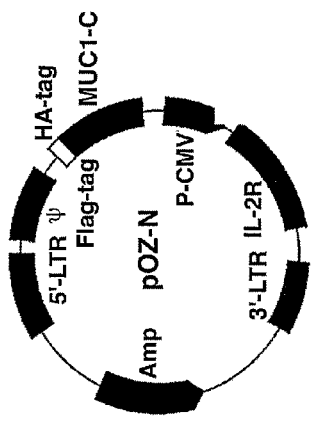
FIG. 1A is a representation of the pOZ-N-MUC1 vector. To construct this vector, MUC1-C was cloned into the retroviral pOZ-N vector downstream of the Flag-HA epitopes.

MUC1 is a mucin-type glycoprotein that is expressed on the apical borders of normal secretory epithelial cells (Kufe et al., 1984). MUC1 forms a heterodimer following synthesis as a single polypeptide and cleavage of the precursor into two subunits in the endoplasmic reticulum (Ligtenberg et al., 1992). The cleavage may be mediated by an autocatalytic process (Levitan et al., 2005). The >250 kDa MUC1 N-terminal (MUC1 N-ter, MUC1-N) subunit contains variable numbers of 20 amino acid tandem repeats that are imperfect with highly conserved variations and are modified by O-linked glycans (Gendler et al., 1988; Siddiqui et al., 1988). MUC1-N is tethered to the cell surface by dimerization with the ~23 kDa C-terminal subunit (MUC1 C-ter, MUC1-C), which includes a 58 amino acid extracellular region, a 28 amino acid transmembrane domain and a 72 amino acid cytoplasmic domain (CD; SEQ ID NO: 1) (Merlo et al., 1989). The human MUC1 sequence is The human MUC1-C sequence is:

GSVVVQLTLAFREGTINVHDVETQFNQYKTEAASRYNLTISDVSVSDVPF

PFSAQSGAGVPGWGIALLVLVCVLVALAIVYLIALAVCQCRRKNYGQLDI

FPARDTYHPMSEYPTYHTHGRYVPPSSTDRSPYEKVSAGNGGSSLSYTNP

AVAATSANL (SEQ ID NO: 5)

With transformation of normal epithelia to carcinomas, MUC1 is aberrantly overexpressed in the cytosol and over the entire cell membrane (Kufe et al., 1984; Perey et al., 1992). Cell membrane-associated MUC1 is targeted to endosomes by clathrin-mediated endocytosis (Kinlough et al., 2004). In addition, MUC1-C, but not MUC1-N, is targeted to the nucleus (Baldus et al., 2004; Huang et al., 2003; Li et al., 2003a; Li et al., 2003b; Li et al., 2003c; Wei et al., 2005; Wen et al., 2003) and mitochondria (Ren et al., 2004).

MUC1 interacts with members of the ErbB receptor family (Li et al., 2001b; Li et al., 2003c; Schroeder et al., 2001) and with the Wnt effector, β-catenin (Yamamoto et al., 1997). The epidermal growth factor receptor and c-Src phosphorylate the MUC1 cytoplasmic domain (MUC1-CD) on Y-46 and thereby increase binding of MUC1 and β-catenin (Li et al., 2001a; Li et al., 2001b). Binding of MUC1 and β-catenin is also regulated by glycogen synthase kinase 3β and protein kinase Cδ (Li et al., 1998; Ren et al., 2002). MUC1 colocalizes with β-catenin in the nucleus (Baldus et al., 2004; Li et al., 2003a; Li et al., 2003c; Wen et al., 2003) and coactivates transcription of Wnt target genes (Huang et al., 2003). Other studies have shown that MUC1 also binds directly to p53 and regulates transcription of p53-target genes (Wei et al., 2005). Notably, overexpression of MUC1 is sufficient to induce anchorage-independent growth and tumorigenicity (Huang et al., 2003; Li et al., 2003b; Ren et al., 2002; Schroeder et al., 2004).

Most mitochondrial proteins are encoded in the nucleus and are imported into mitochondria by translocation complexes in the outer and inner mitochondrial membranes. Certain mitochondrial proteins contain N-terminal mitochondrial targeting sequences and interact with Tom20 in the outer mitochondrial membrane (Truscott et al., 2003). Other mitochondrial proteins contain internal targeting sequences and interact with the Tom70 receptor (Truscott et al., 2003). Recent work showed that mitochondrial proteins without internal targeting sequences are delivered to Tom70 by a complex of HSP70 and HSP90 (Young et al., 2003).

The studies described below show, using tandem affinity purification of MUC1 complexes and MALDI-TOF-MS, that MUC1 forms intracellular complexes with HSP70 and HSP90. These results were confirmed by showing that MUC1 at the cell membrane and in the cytosol coprecipitates with HSP70 and HSP90 and that the MUC1 cytoplasmic tail is sufficient for conferring the association with HSP70 and HSP90 in cells. Moreover, MUC1-CD interacted with HSP70 and HSP90 in vitro. These findings indicate that MUC1 forms complexes with HSP70 and HSP90, and that these chaperones contribute to mitochondrial targeting of MUC1.

The human HSP70 sequence is:

```
  1 msvvgidlgf qscyvavara ggietianey sdrctpacis fgpknrsiga aaksqvisna
 61 kntvqgfkrf hgrafsdpfv eaeksnlayd ivqwptgltg ikvtymeeer nftteqvtam
121 llsklketae svlkkpvvdc vvsvpcfytd aerrsvmdat qiaglnclrl mnettavala
```

-continued

```
181 ygiykqdlpr leekprnvvf vdmghsayqv svcafnrgkl kvlatafdtt lggrkfdevl 241 vnhfceefgk kykldikski rallrlsqec eklkklmsan asdlplsiec fmndvdvsgt 301 mnrgkflemc ndllarvepp lrsvleqtkl kkediyavei vggatripav kekiskffgk 361 elsttlnade avtrgcalqc ailspafkvr efsitdvvpy pislrwnspa eegssdcevf 421 sknhaapfsk vltfyrkepf tleayysspq dlpypdpaia qfsvqkvtpq sdgssskvkv 481 kvrvnvhgif svssaslvev hkseeneepm etdqnakeee kmqvdqeeph veeqqqtpa 541 enkaeseeme tsqagskdkk mdqppqcqeg ksedqycgpa nresaiwqid remlnlyien 601 egkmimqdkl ekerndakna veeyvyemrd klsgeyekfv seddrnsftl kledtenwly 661 edgedqpkqv yvdklaelkn lgqpikirfq eseerpnylk n (SEQ ID NO: 3)
```

The human HSP90 sequence is:

```
  1 mpeevhhgee evetfafqae iaqlmsliin tfysnkeifl relisnasda ldkiryeslt 61 dpskldsgke lkidiipnpq ertltlvdtg igmtkadlin nlgtiaksgt kafmealqag 121 adismigqfg vgfysaylva ekvvvirkhn ddeqyawess aggsftvrad hgepigmgtk 181 vilhlkedqt eyleerrvke vvkkhsqfig ypitlyleke rekeisddea eeekgekeee 241 dkddeekpki edvgsdeedd sgkdkkkktk kikekyidqe elnktkpiwt rnpdditqee 301 ygefyksltn dwedhlavkh fsvegqlefr allfiprrap fdlfenkkkk nniklyvrrv 361 fimdscdeli peylnfirgv vdsedlplni sremlqqski lkvirknivk kclelfsela 421 edkenykkfy eafsknlklg ihedstnrrr lsellryhts qsgdemtsls eyvsrmketq 481 ksiyyitges keqvansafv ervrkrgfev vymtepidey cvqqlkefdg kslvsvtkeg 541 lelpedeeek kkmeeskakf enlcklmkei ldkkvekvti snrlvsspcc ivtstygwta 601 nmerimkaqa lrdnstmgym makkhleinp dhpivetlrq kaeadkndka vkdlvvllfe 661 tallssgfsl edpqthsnri yrmiklglgi dedevaaeep naavpdeipp legdedasrm 721 eevd (SEQ ID NO: 4)
```

MUC1-C and not MUC1-N is targeted to mitochondria, and this targeting is stimulated by HRG (Ren et al., 2004). Moreover, constitutive and HRG-induced targeting of MUC1-C to mitochondria are both attenuated by the Y46F mutation (Ren et al., 2004). In this context, c-Src is activated by HRG (Belsches-Jablonski et al., 2001; Vadlamudi et al., 2003), and c-Src phosphorylates MUC1 on Y-46 (Li et al., 2001a). The present results show that the MUC1 cytoplasmic domain (MUC1-CD) binds to HSP70 and that this interaction occurs independently of c-Src or HRG stimulation. By contrast, binding of MUC1 to HSP90 in vitro was dependent on c-Src. In cells, it was found that MUC1 binds constitutively to HSP90, presumably because of basal levels of Y-46 phosphorylation, and that c-Src stimulates this interaction. Moreover, HRG stimulation, which activates c-Src, increased the interaction between MUC1 and HSP90 by a mechanism that was attenuated by PP2 or by expressing MUC1 with the Y46F mutation. These results collectively support a model in which MUC1 binds constitutively to HSP70 and that, with HRG-induced activation of c-Src, phosphorylation of MUC1 on Y-46 in turn stimulates the interaction with HSP90 (FIG. 7D). PP2 also attenuated HRG-induced targeting of MUC1 to mitochondria, a finding in concert with the role of c-Src in inducing MUC1 binding to HSP90 for delivery to the mitochondrial surface.

The in vitro binding data described below indicate that HSP70 binds to the MUC1 cytoplasmic tail in the same region as β-catenin. These data suggested that MUC1 may form exclusive complexes with β-catenin and with HSP70. In this regard, there was no detectable β-catenin associated with MUC1 that was delivered to the mitochondrial outer membrane. These findings collectively support a model in which c-Src phosphorylation regulates HSP90 binding to the client MUC1 protein for delivery to mitochondria.

Figure 7C:
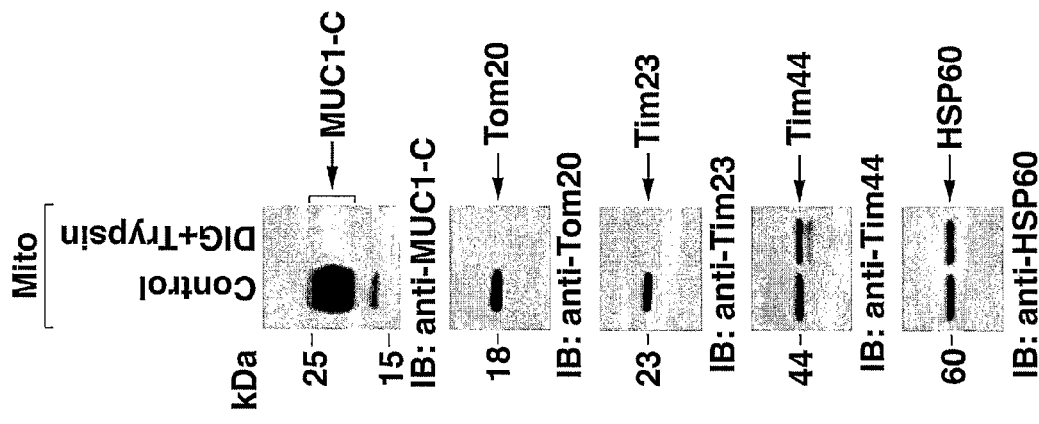
FIG. 7C is a series of immunoblots of purified mitochondria from HCT116/MUC1 cells that were treated with 0.5% digitonin for 1 minute at 4° C., diluted with buffer, and then digested with 60 mg/ml trypsin for 15 minutes at 4° C. Digestion of the proteins was analyzed by immunoblotting with the indicated antibodies.
Figure 8:
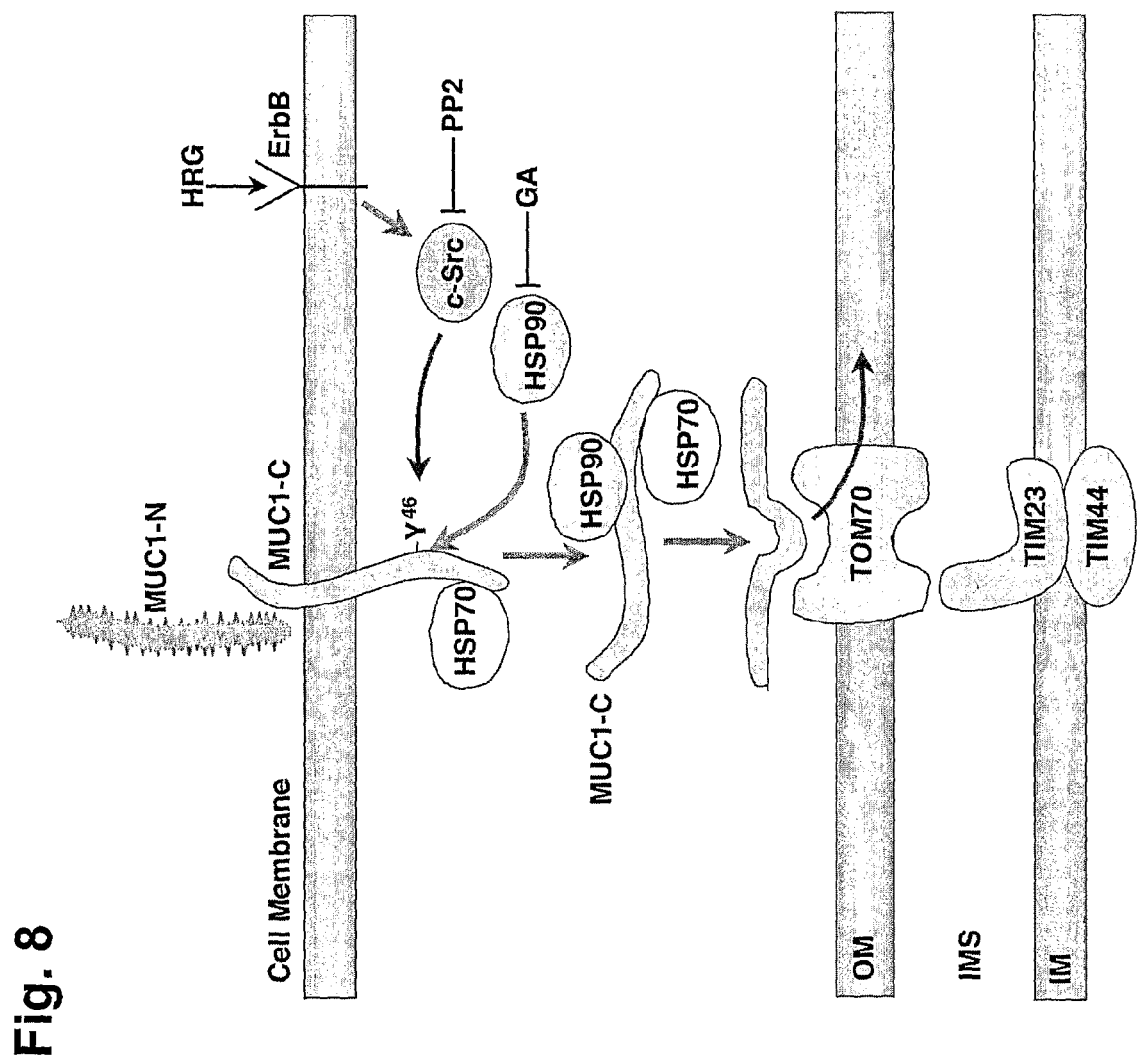
FIG. 8 is a depiction of a proposed pathway for targeting of MUC1 to mitochondria by HRG/ErbB receptor/c-Src signaling and the HSP70/HSP90 complex. TOM, translocase of the mitochondrial outer membrane. TIM, translocase of the mitochondrial inner membrane.

MUC1 is targeted for integration into the mitochondrial outer membrane. HSP70 functions in the folding of newly synthesized proteins (Bukau et al., 2000; Hartl & Hayer-Hartl, 2002) and cooperates with HSP90 in targeting preproteins to the mitochondrial receptor Tom70 (Young et al., 2003). Binding of HSP70 and HSP90 to Tom70 are in turn required for preprotein import (Young et al., 2003). GA, an inhibitor of the ATP-driven HSP90 chaperone cycle (Young & Hartl, 2000), attenuated HRG-induced binding of MUC1 to HSP90 and targeting of MUC1 to mitochondria, consistent with delivery by a HSP90-dependent mechanism (FIG. 7D). In further support of HSP90-mediated delivery, GA decreased the constitutive localization of MUC1 to mitochondria without affecting total intracellular MUC1 pools. In previous work, treatment of purified mitochondria with trypsin had no effect on MUC1 (Ren et al., 2004). Moreover, analysis of purified mitochondria incubated in alkaline sodium carbonate indicated that MUC1 is an integral membrane protein (Ren et al., 2004). In the present studies, mitochondria were treated with hypotonic buffer to disrupt the outer membrane (Ryan et al., 2001). Under these conditions, trypsin had no effect on MUC1, but decreased Tim23, a mitochondrial inner membrane protein that is exposed in the inter membrane space (Moro et al., 1999). Mitochondria were also treated with low levels of digitonin to selectively permeabilize the outer membrane. Permeabilization per se had no effect, but when combined with trypsin was associated with digestion of MUC1. As controls, this approach also resulted in digestion of Tim23, but had little effect on Tim44 which is buried in the matrix face of the mitochondrial inner membrane (Truscott et al., 2003; Wada & Kanwar, 1998). These findings thus collectively support integration and embedding of MUC1 into the mitochondrial outer membrane (FIG. 8). MUC1 attenuates release of mitochondrial apoptogenic factors in the response to stress (Ren et al., 2004). However, integration of MUC1 into the mitochondrial outer membrane could interfere with localization of the proapoptotic Bcl-2 subfamily members and thereby neutralization of the antiapoptotic Bcl-2/Bcl-XL proteins.

In summary, the above results demonstrate that binding of HSP70 and HSP90 results in localization of MUC1-C to the mitochondria. Mitochondrial MUC1 suppresses apoptosis, e.g., stress-induced apoptosis.

Since MUC1 becomes associated with HSP70 and HSP90 via its physical association with these proteins, compounds that ablate, or at least inhibit, the interaction between MUC1 and HSP70 and/or HSP90 are likely to be useful for enhancing the intrinsic apoptosis of cancer cells and also the cancer cell cytocidal effects of genotoxic agents such as ionizing radiation and chemotherapeutic drugs. Moreover, such compounds could also be useful as prophylactic agents in subjects that have an increased risk (due, for example, to genetic, physiological, or environmental factors) of the development of a malignancy.

Methods of Screening for Inhibitory Compounds

The invention provides in vitro methods for identifying compounds (small molecules or macromolecules) that inhibit binding of MUC1-binders (HSP70 and HSP90) to MUC1.

These methods can be performed using: (a) isolated MUC1 test agents and MUC1-binder test agents; or (b) cells expressing a MUC1 test agent and one or both MUC1-binder test agents.

The term "isolated" as applied to any of the above-listed polypeptide test agents refers to a polypeptide, or a peptide fragment thereof, which either has no naturally-occurring counterpart or has been separated or purified from components which naturally accompany it, e.g., in tissues such as pancreas, liver, spleen, ovary, testis, muscle, joint tissue, neural tissue, gastrointestinal tissue or tumor tissue (e.g., breast cancer or colon cancer tissue), or body fluids such as blood, serum, or urine. Typically, the polypeptide or peptide fragment is considered "isolated" when it is at least 70%, by dry weight, free from the proteins and other naturally-occurring organic molecules with which it is naturally associated. Preferably, a preparation of a test agent is at least 80%, more preferably at least 90%, and most preferably at least 99%, by dry weight, the test agent. Since a polypeptide that is chemically synthesized is, by its nature, separated from the components that naturally accompany it, a synthetic polypeptide test agent is "isolated."

An isolated polypeptide test agent can be obtained, for example, by extraction from a natural source (e.g., from tissues); by expression of a recombinant nucleic acid encoding the polypeptide; or by chemical synthesis. A polypeptide test agent that is produced in a cellular system different from the source from which it naturally originates is "isolated," because it will necessarily be free of components which naturally accompany it. The degree of isolation or purity can be measured by any appropriate method, e.g., column chromatography, polyacrylamide gel electrophoresis, or HPLC analysis.

Prior to testing, any of the test agents can undergo modification, e.g., phosphorylation or glycosylation, by methods known in the art. For example, a MUC1 test agent can be phosphorylated by c-Src.

In methods of screening for compounds that inhibit or enhance binding of an isolated MUC1 test agent to an isolated MUC1-binder test agent, a MUC1 test agent is contacted with a MUC1-binder test agent in the presence of one or more concentrations of a test compound and binding between the two test agents in the presence and absence of the test compound is detected and/or measured. In such assays neither of the test agents need be detectably labeled. For example, by exploiting the phenomenon of surface plasmon resonance, the MUC1 test agent can be bound to a suitable solid substrate and the MUC1-binder test agent exposed to the substrate-bound MUC1 test agent in the presence and absence of the compound of interest. Binding of the MUC1-binder test agent to the MUC1 test agent on the solid substrate results in a change in the intensity of surface plasmon resonance that can be detected qualitatively or quantitatively by an appropriate instrument, e.g., a Biacore™ apparatus (Biacore International AB, Rapsgatan, Sweden). It will be appreciated that the experiment can be performed in reverse, i.e., with the MUC1-binder test agent bound to the solid substrate and the MUC1 test agent added to it in the presence of the test compound.

Moreover, assays to test for inhibition or enhancement of binding to MUC1 can involve the use, for example, of: (a) a single MUC1-specific "detection" antibody that is detectably labeled; (b) an unlabeled MUC1-specific antibody and a detectably labeled secondary antibody; or (c) a biotinylated MUC1-specific antibody and detectably labeled avidin. In addition, combinations of these approaches (including "multi-layer" assays) familiar to those in the art can be used to enhance the sensitivity of assays. In these assays, the MUC1-binder test agent can be immobilized on a solid substrate such as a nylon or nitrocellulose membrane by, for example, "spotting" an aliquot of a sample containing the test agent onto a membrane or by blotting onto a membrane an electrophoretic gel on which the sample or an aliquot of the sample has been subjected to electrophoretic separation. Alternatively, the MUC1-binder test agent can be bound to a plastic substrate (e.g., the plastic bottom of an ELISA (enzyme-linked immunosorbent assay) plate well using methods known in the art. The substrate-bound test agent is then exposed to the MUC1 test agent in the presence and absence of the test compound. After incubating the resulting mixture for a period of time and at temperature optimized for the system of interest, the presence and/or amount of MUC1 test agent bound to the MUC1-binder test on the solid substrate is then assayed using a detection antibody that binds to the MUC1 test agent and, where required, appropriate detectably labeled secondary antibodies or avidin. It will be appreciated that instead of binding the MUC1-binder test agent to the solid substrate, the MUC1 test agent can be bound to it. In this case binding of the MUC1-binder test agent to the substrate-bound MUC1 is tested by obvious adaptations of the method described above for substrate-bound MUC1-binder test agent.

The invention also features "sandwich" assays. In these sandwich assays, instead of immobilizing test agents on solid substrates by the methods described above, an appropriate test agent can be immobilized on the solid substrate by, prior to exposing the solid substrate to the test agent, conjugating a "capture" test agent-specific antibody (polyclonal or mAb) to the solid substrate by any of a variety of methods known in the art. The test agent is then bound to the solid substrate by virtue of its binding to the capture antibody conjugated to the solid substrate. The procedure is carried out in essentially the same manner described above for methods in which the appropriate test agent is bound to the solid substrate by techniques not involving the use of a capture antibody. It is understood that in these sandwich assays, the capture antibody should not bind to the same epitope (or range of epitopes in the case of a polyclonal antibody) as the detection antibody. Thus, if a mAb is used as a capture antibody, the detection antibody can be either: (a) another mAb that binds to an epitope that is either completely physically separated from or only partially overlaps with the epitope to which the capture mAb binds; or (b) a polyclonal antibody that binds to epitopes other than or in addition to that to which the capture mAb binds. On the other hand, if a polyclonal antibody is used as a capture antibody, the detection antibody can be either (a) a mAb that binds to an epitope that is either completely physically separated from or partially overlaps with any of the epitopes to which the capture polyclonal antibody binds; or (b) a polyclonal antibody that binds to epitopes other than or in addition to that to which the capture polyclonal antibody binds. Assays that involve the use of a capture and a detection antibody include sandwich ELISA assays, sandwich Western blotting assays, and sandwich immunomagnetic detection assays.

Suitable solid substrates to which the capture antibody can be bound include, without limitation, the plastic bottoms and sides of wells of microtiter plates, membranes such as nylon or nitrocellulose membranes, polymeric (e.g., without limitation, agarose, cellulose, or polyacrylamide) beads or particles.

Methods of detecting and/or for quantifying a detectable label depend on the nature of the label and are known in the art. Appropriate labels include, without limitation, radionuclides (e.g., $^{125}I$, $^{131}I$, $^{35}S$, $^{3}H$, $^{32}P$, or $^{14}C$), fluorescent moieties (e.g., fluorescein, rhodamine, or phycoerythrin), luminescent moieties (e.g., Qdot™ nanoparticles supplied by the Quantum Dot Corporation, Palo Alto, Calif.), compounds that absorb light of a defined wavelength, or enzymes (e.g., alkaline phosphatase or horseradish peroxidase). The products of reactions catalyzed by appropriate enzymes can be, without limitation, fluorescent, luminescent, or radioactive or they may absorb visible or ultraviolet light. Examples of detectors include, without limitation, x-ray film, radioactivity counters, scintillation counters, spectrophotometers, calorimeters, fluorometers, luminometers, and densitometers.

Candidate compounds can also be tested for their ability to inhibit or enhance binding of MUC1 to a MUC1-binder in cells. The cells can either naturally express an appropriate MUC1 test agent and/or MUC1-binder test agent of interest or they can recombinantly express either or both test agents. The cells can be normal or malignant and of any histological type, e.g., without limitation, epithelial cells, fibroblasts, lymphoid cells, macrophages/monocytes, granulocytes, keratinocytes, or muscle cells. Suitable cell lines include those recited in the examples, e.g., breast cancer or colon cancer cell lines. The test compound can be added to the solution (e.g., culture medium) containing the cells or, where the compound is a protein, the cells can recombinantly express it. The cells can optionally also be exposed to a stimulus of interest (e.g., a growth factor such as EGF) prior to or after exposure of the cells to the compound. Following incubation of cells expressing the test agents of interest in the absence or presence (optionally at various concentrations), physical association between the test agents can be determined microscopically using appropriately labeled antibodies specific for both test agents, e.g., by confocal microscopy. Alternatively, the cells can be lysed under non-dissociating conditions and the lysates tested for the presence of physically associated test agents. Such methods include adaptations of those described using isolated test agents. For example, an antibody specific for one of the two test agents (test agent 1) can be bound to a solid substrate (e.g., the bottom and sides of the well of a microtiter plate or a nylon membrane). After washing away unbound antibody, the solid substrate with bound antibody is contacted with the cell lysate. Any test agent 1 in the lysate, bound or not bound to the second test agent (test agent 2), will bind to the antibody specific for test agent 1 on the solid substrate. After washing away unbound lysate components, the presence of test agent 2 (bound via test agent 1 and the antibody specific for test agent 1 to the solid substrate) is tested for using a detectably labeled antibody (see above) specific for test agent 2. Alternatively, test agent 1 can be immunoprecipitated with an antibody specific for test agent 1 and the immunoprecipitated material can be subjected to electrophoretic separation (e.g., by polyacrylamide gel electrophoresis performed under non-dissociating conditions). The electrophoretic gel can then be blotted onto a membrane (e.g., a nylon or a nitrocellulose membrane) and any test agent 2 on the membrane detected and/or measured with a detectably labeled antibody (see above) specific for test agent 2 by any of the above-described methods. It is understood that in the above-described assays, test agent 1 can be either the MUC1 test agent or the MUC1-binder test agent or vice versa.

Compounds which may be screened using the assay methods described herein may be natural or synthetic chemical compounds. Extracts of plants, microbes or other organisms that contain several characterized or uncharacterized components may also be used. Combinatorial libraries (including solid phase synthesis and parallel synthesis methodologies) provide an efficient means for screening a large numbers of different substances.

Methods of Designing and Producing Inhibitory Compounds

The invention also relates to using MUC1 test agents and/or MUC1-binder test agents to predict or design compounds that can interact with MUC1 and/or MUC1-binders and potentially thereby inhibit the ability of MUC1 to interact with an appropriate MUC1-binder. One of skill in the art would know how to use standard molecular modeling or other techniques to identify small molecules that would bind to "appropriate sites" on MUC1 and/or MUC1-binders. One such example is provided in Broughton (1997) Curr. Opin. Chem. Biol. 1:392-398. Typically, an "appropriate site" on a MUC1 or MUC1-binder is a site directly involved in the physical interaction between the two molecule types. However, an "appropriate site" can also be an allosteric site, i.e., a region of the molecule not directly involved in a physical interaction with another molecule (and possibly even remote from such a "physical interaction" site) but to which binding of a compound results (e.g., by the induction in a conformational change in the molecule) in inhibition of the binding of the molecule to another molecule By "molecular modeling" is meant quantitative and/or qualitative analysis of the structure and function of protein-protein physical interaction based on three-dimensional structural information and protein-protein interaction models. This includes conventional numeric-based molecular dynamic and energy minimization models, interactive computer graphic models, modified molecular mechanics models, distance geometry and other structure-based constraint models. Molecular modeling typically is performed using a computer and may be further optimized using known methods.

Methods of designing compounds that bind specifically (e.g., with high affinity) to the region of MUC1 that interacts with HSP70 and/or HSP90 (i.e., the cytoplasmic domain of MUC1) or the regions of HSP70 and HSP90 that bind to MUC1 (i.e., the substrate binding domains) typically are also computer-based, and involve the use of a computer having a program capable of generating an atomic model. Computer programs that use X-ray crystallography data are particularly useful for designing such compounds. Programs such as RasMol, for example, can be used to generate a three dimensional model of, e.g., the region of MUC1 that interacts with HSP70 or HSP90 or the region of HSP70 or HSP90 that binds to MUC1 and/or determine the structures involved in MUC1-HSP70 or MUC1-HSP90 binding. Computer programs such as INSIGHT (Accelrys, Burlington, Mass.), GRASP (Anthony Nicholls, Columbia University), Dock (Molecular Design Institute, University of California at San Francisco), and Auto-Dock (Accelrys) allow for further manipulation and the ability to introduce new structures.

Compounds can be designed using, for example, computer hardware or software, or a combination of both. However, designing is preferably implemented in one or more computer programs executing on one or more programmable computers, each containing a processor and at least one input device. The computer(s) preferably also contain(s) a data storage system (including volatile and non-volatile memory and/or storage elements) and at least one output device. Program code is applied to input data to perform the functions described above and generate output information. The output information is applied to one or more output devices in a known fashion. The computer can be, for example, a personal computer, microcomputer, or work station of conventional design.

Each program is preferably implemented in a high level procedural or object oriented programming language to communicate with a computer system. However, the programs can be implemented in assembly or machine language, if desired. In any case, the language can be a compiled or interpreted language.

Each computer program is preferably stored on a storage media or device (e.g., ROM or magnetic diskette) readable by a general or special purpose programmable computer. The computer program serves to configure and operate the computer to perform the procedures described herein when the program is read by the computer. The method of the invention can also be implemented by means of a computer-readable storage medium, configured with a computer program, where the storage medium so configured causes a computer to operate in a specific and predefined manner to perform the functions described herein.

For example, the computer-requiring steps in a method of designing a compound can involve:

(a) inputting into an input device, e.g., through a keyboard, a diskette, or a tape, data (e.g. atomic coordinates) that define the three-dimensional (3-D) structure of a first molecule (e.g., MUC1 or a part of MUC1, or MUC1 or a part of MUC1 that is phosphorylated on a tyrosine residue) that binds to a second molecule (e.g., a MUC1-binder or a part thereof) or a molecular complex (e.g., MUC1, or a part thereof, bound to a MUC1-binder, or a part thereof), e.g., a region of MUC1 that interacts with HSP70 or HSP90 (i.e., the cytoplasmic domain of MUC1), the region of HSP70 or HSP90 that binds to MUC1 (i.e., the substrate binding domain), or all or a part (e.g., the cytoplasmic domain) of MUC1 bound to all or a part of HSP70 or HSP90; and (b) determining, using a processor, the 3-D structure (e.g., an atomic model) of: (i) the site on the first molecule involved in binding to the second molecule; or (ii) one or more sites on the molecular components of molecular complex of interaction between molecular components of the molecular complex.

From the information obtained in this way, one skilled in the art will be able to design and make inhibitory compounds (e.g., peptides, non-peptide small molecules, aptamers (e.g., nucleic acid aptamers) with the appropriate 3-D structure (see "Methods of Making Inhibitory Compounds and Proteins Useful for the Invention" below).

Moreover, if computer-usable 3-D data (e.g., x-ray crystallographic data) for a candidate compound are available, the following computer-based steps can be performed in conjunction with computer-based steps (a) and (b) described above:

(c) inputting into an input device, e.g., through a keyboard, a diskette, or a tape, data (e.g. atomic coordinates) that define the three-dimensional (3-D) structure of a candidate compound;

(d) determining, using a processor, the 3-D structure (e.g., an atomic model) of the candidate compound;

(e) determining, using the processor, whether the candidate compound binds to the site on the first molecule or the one or more sites on the molecular components of the molecular complex; and (f) identifying the candidate compound as compound that inhibits the interaction between the first and second molecule or between the molecular components of the molecular complex.

The method can involve the additional step of outputting to an output device a model of the 3-D structure of the compound. In addition, the 3-D data of candidate compounds can be compared to a computer database of, for example, 3-D structures (e.g., of MUC1, the cytoplasmic domain of MUC1, p53, or the regulatory domain of p53) stored in a data storage system.

Compounds of the invention also may be interactively designed from structural information of the compounds described herein using other structure-based design/modeling techniques (see, e.g., Jackson (1997) *Seminars in Oncology* 24:L164-172; and Jones et al. (1996) *J. Med. Chem.* 39:904-917). Compounds and polypeptides of the invention also can be identified by, for example, identifying candidate compounds by computer modeling as fitting spatially and preferentially (i.e., with high affinity) into the appropriate acceptor sites on MUC1, HSP70, or HSP90.

Candidate compounds identified as described above can then be tested in standard cellular or cell-free binding or binding inhibition assays familiar to those skilled in the art. Exemplary assays are described herein.

A candidate compound whose presence requires at least 2-fold (e.g., 4-fold, 6-fold, 10-fold, 100-fold, 1000-fold, 10,000 fold, or 100,000-fold) more of a given MUC1 test agent to achieve a defined arbitrary level of binding to a fixed amount of a MUC1-binder test agent than is achieved in the absence of the compound can be useful for inhibiting the interaction between MUC1 and the relevant MUC1-binder, and thus can be useful as a cancer therapeutic or prophylactic agent. Alternatively, a candidate compound whose presence requires at least 2-fold (e.g., 2-fold, 4-fold, 6-fold, 10-fold, 100-fold, 1000-fold, 10,000 fold, or 100,000-fold) more of a given MUC1-binder test agent to achieve a defined arbitrary level of binding to a fixed amount of a MUC1 test agent than is achieved in the absence of the compound can be useful for inhibiting the interaction between MUC1 and the relevant MUC1-binder, and thus can be useful as a cancer therapeutic or prophylactic agent.

The 3-D structure of biological macromolecules (e.g., proteins, nucleic acids, carbohydrates, and lipids) can be determined from data obtained by a variety of methodologies. These methodologies, which have been applied most effectively to the assessment of the 3-D structure of proteins, include: (a) x-ray crystallography; (b) nuclear magnetic resonance (NMR) spectroscopy; (c) analysis of physical distance constraints formed between defined sites on a macromolecule, e.g., intramolecular chemical crosslinks between residues on a protein (e.g., International Patent Application No. PCT/US00/14667, the disclosure of which is incorporated herein by reference in its entirety), and (d) molecular modeling methods based on a knowledge of the primary structure of a protein of interest, e.g., homology modeling techniques, threading algorithms, or ab initio structure modeling using computer programs such as MONSSTER (Modeling Of New Structures from Secondary and Tertiary Restraints) (see, e.g., International Application No. PCT/US99/11913, the disclosure of which is incorporated herein by reference in its entirety). Other molecular modeling techniques may also be employed in accordance with this invention (e.g., Cohen et al. (1990) J. Med. Chem. 33:883-894; Navia et al. (1992) Curr. Opin. Struct. Biol. 2: 202-210, the disclosures of which are incorporated herein by reference in their entirety). All these methods produce data that are amenable to computer analysis. Other spectroscopic methods that can also be useful in the method of the invention, but that do not currently provide atomic level structural detail about biomolecules, include circular dichroism and fluorescence and ultraviolet/visible light absorbance spectroscopy. A preferred method of analysis is x-ray crystallography. Descriptions of this procedure and of NMR spectroscopy are provided below.

X-Ray Crystallography

X-ray crystallography is based on the diffraction of x-radiation of a characteristic wavelength by electron clouds surrounding the atomic nuclei in a crystal of a molecule or molecular complex of interest. The technique uses crystals of purified biological macromolecules or molecular complexes (but these frequently include solvent components, co-factors, substrates, or other ligands) to determine near atomic resolution of the atoms making up the particular biological macromolecule. A prerequisite for solving 3-D structure by x-ray crystallography is a well-ordered crystal that will diffract x-rays strongly. The method directs a beam of x-rays onto a regular, repeating array of many identical molecules so that the x-rays are diffracted from the array in a pattern from which the structure of an individual molecule can be retrieved. Well-ordered crystals of, for example, globular protein molecules are large, spherical or ellipsoidal objects with irregular surfaces. The crystals contain large channels between the individual molecules. These channels, which normally occupy more than one half the volume of the crystal, are filled with disordered solvent molecules, and the protein molecules are in contact with each other at only a few small regions. This is one reason why structures of proteins in crystals are generally the same as those of proteins in solution.

Methods of obtaining the proteins of interest are described below. The formation of crystals is dependent on a number of different parameters, including pH, temperature, the concentration of the biological macromolecule, the nature of the solvent and precipitant, as well as the presence of added ions or ligands of the protein. Many routine crystallization experiments may be needed to screen all these parameters for the combinations that give a crystal suitable for x-ray diffraction analysis. Crystallization robots can automate and speed up work of reproducibly setting up a large number of crystallization experiments (see, e.g., U.S. Pat. No. 5,790,421, the disclosure of which is incorporated herein by reference in its entirety).

Polypeptide crystallization occurs in solutions in which the polypeptide concentration exceeds its solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Crystallizations are generally carried out between 4° C. and 20° C. Substances known as "precipitants" are often used to decrease the solubility of the polypeptide in a concentrated solution by forming an energetically unfavorable precipitating depleted layer around the polypeptide molecules (Weber (1991) Advances in Protein Chemistry 41:1-36). In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-2-4 pentanediol, and many of the polyglycols, such as polyethylene glycol (PEG). The precipitating solutions can include, for example, 13-24% PEG 4000, 5-41% ammonium sulfate, and 1.0-1.5 M sodium chloride, and a pH ranging from 5.0-7.5. Other additives can include 0.1 M Hepes, 2-4% butanol, 20-100 mM sodium acetate, 50-70 mM citric acid, 120-130 mM sodium phosphate, 1 mM ethylene diamine tetraacetic acid (EDTA), and 1 mM dithiothreitol (DTT). These agents are prepared in buffers and are added dropwise in various combinations to the crystallization buffer. Proteins to be crystallized can be modified, e.g., by phosphorylation or by using a phosphate mimic (e.g., tungstate, cacodylate, or sulfate).

Commonly used polypeptide crystallization methods include the following techniques: batch, hanging drop, seed initiation, and dialysis. In each of these methods, it is important to promote continued crystallization after nucleation by maintaining a supersaturated solution. In the batch method, polypeptide is mixed with precipitants to achieve supersaturation, and the vessel is sealed and set aside until crystals appear. In the dialysis method, polypeptide is retained in a sealed dialysis membrane that is placed into a solution containing precipitant. Equilibration across the membrane increases the polypeptide and precipitant concentrations, thereby causing the polypeptide to reach supersaturation levels.

In the preferred hanging drop technique (McPherson (1976) J. Biol. Chem., 251:6300-6306), an initial polypeptide mixture is created by adding a precipitant to a concentrated polypeptide solution. The concentrations of the polypeptide and precipitants are such that in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the second solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide may form.

Another method of crystallization introduces a nucleation site into a concentrated polypeptide solution. Generally, a concentrated polypeptide solution is prepared and a seed crystal of the polypeptide is introduced into this solution. If the concentrations of the polypeptide and any precipitants are correct, the seed crystal will provide a nucleation site around which a larger crystal forms.

Yet another method of crystallization is an electrocrystallization method in which use is made of the dipole moments of protein macromolecules that self-align in the Helmholtz layer adjacent to an electrode (see, e.g., U.S. Pat. No. 5,597,457, the disclosure of which is incorporated herein by reference in its entirety).

Some proteins may be recalcitrant to crystallization. However, several techniques are available to the skilled artisan to induce crystallization. For example, the removal of flexible polypeptide segments at the amino or carboxyl terminal end of the protein may facilitate production of crystalline protein samples. Removal of such segments can be done using molecular biology techniques or treatment of the protein with proteases such as trypsin, chymotrypsin, or subtilisin.

In diffraction experiments, a narrow and parallel beam of x-rays is taken from the x-ray source and directed onto the crystal to produce diffracted beams. The incident primary beams cause damage to both the macromolecule and solvent molecules. The crystal is, therefore, cooled (e.g., to between −220° C. and −50° C.) to prolong its lifetime. The primary beam must strike the crystal from many directions to produce all possible diffraction spots, so the crystal is rotated in the beam during the experiment. The diffracted spots are recorded on a film or by an electronic detector. Exposed film has to be digitized and quantified in a scanning device, whereas the electronic detectors feed the signals they detect directly into a computer. Electronic area detectors significantly reduce the time required to collect and measure diffraction data. Each diffraction beam, which is recorded as a spot on film or a detector plate, is defined by three properties: the amplitude, which is measured from the intensity of the spot; the wavelength, which is set by the x-ray source; and the phase, which is lost in x-ray experiments. All three properties are needed for all of the diffracted beams in order to determine the positions of the atoms giving rise to the diffracted beams. One way of determining the phases is called Multiple Isomorphous Replacement (MIR), which requires the introduction of exogenous x-ray scatterers (e.g., heavy atoms such metal atoms) into the unit cell of the crystal. For a more detailed description of MIR, see U.S. Pat. No. 6,093,573 (column 15), the disclosure of which is incorporated herein by reference in its entirety.

Atomic coordinates refer to Cartesian coordinates (x, y, and z positions) derived from mathematical equations involving Fourier synthesis of data derived from patterns obtained via diffraction of a monochromatic beam of x-rays by the atoms (scattering centers) of biological macromolecule of interest in crystal form. Diffraction data are used to calculate electron density maps of repeating units in the crystal (unit cell). Electron density maps are used to establish the positions (atomic coordinates) of individual atoms within a crystal's unit cell. The absolute values of atomic coordinates convey spatial relationships between atoms because the absolute values ascribed to atomic coordinates can be changed by rotational and/or translational movement along x, y, and/or z axes, together or separately, while maintaining the same relative spatial relationships among atoms. Thus, a biological macromolecule (e.g., a protein) whose set of absolute atomic coordinate values can be rotationally or translationally adjusted to coincide with a set of prior determined values from an analysis of another sample is considered to have the same atomic coordinates as those obtained from the other sample.

Further details on x-ray crystallography can be obtained from co-pending U.S. Application No. 2005/0015232, U.S. Pat. No. 6,093,573 and International Application Nos. PCT/US99/18441, PCT/US99/11913, and PCT/US00/03745. The disclosures of all these patent documents are incorporated herein by reference in their entirety.

NMR Spectroscopy

Whereas x-ray crystallography requires single crystals of a macromolecule of interest, NMR measurements are carried out in solution under near physiological conditions. However, NMR-derived structures are not as detailed as crystal-derived structures.

While the use of NMR spectroscopy was until relatively recently limited to the elucidation of the 3-D structure of relatively small molecules (e.g., proteins of 100-150 amino acid residues), recent advances including isotopic labeling of the molecule of interest and transverse relaxation-optimized spectroscopy (TROSY) have allowed the methodology to be extended to the analysis of much larger molecules, e.g., proteins with a molecular weight of 110 kDa (Wider (2000) BioTechniques, 29:1278-1294).

NMR uses radio-frequency radiation to examine the environment of magnetic atomic nuclei in a homogeneous magnetic field pulsed with a specific radio frequency. The pulses perturb the nuclear magnetization of those atoms with nuclei of nonzero spin. Transient time domain signals are detected as the system returns to equilibrium. Fourier transformation of the transient signal into a frequency domain yields a one-dimensional NMR spectrum. Peaks in these spectra represent chemical shifts of the various active nuclei. The chemical shift of an atom is determined by its local electronic environment. Two-dimensional NMR experiments can provide information about the proximity of various atoms in the structure and in three dimensional space. Protein structures can be determined by performing a number of two- (and sometimes 3- or 4-) dimensional NMR experiments and using the resulting information as constraints in a series of protein folding simulations.

More information on NMR spectroscopy including detailed descriptions of how raw data obtained from an NMR experiment can be used to determine the 3-D structure of a macromolecule can be found in: Protein NMR Spectroscopy, Principles and Practice, J. Cavanagh et al., Academic Press, San Diego, 1996; Gronenborn et al. (1990) Anal. Chem. 62(1):2-15; and Wider (2000), supra., the disclosures of all of which are incorporated herein by reference in their entirety Any available method can be used to construct a 3-D model of a region of MUC1 and/or a MUC1-binder of interest from the x-ray crystallographic and/or NMR data using a computer as described above. Such a model can be constructed from analytical data points inputted into the computer by an input device and by means of a processor using known software packages, e.g., HKL, MOSFILM, XDS, CCP4, SHARP, PHASES, HEAVY, XPLOR, TNT, NMRCOMPASS, NMRPIPE, DIANA, NMRDRAW, FELIX, VNMR, MADIGRAS, QUANTA, BUSTER, SOLVE, O, FRODO, or CHAIN. The model constructed from these data can be visualized via an output device of a computer, using available systems, e.g., Silicon Graphics, Evans and Sutherland, SUN, Hewlett Packard, Apple Macintosh, DEC, IBM, or Compaq.

Methods of Making Inhibitory Compounds and Proteins Useful for the Invention

Once the 3-D structure of a protein of interest (MUC1, HSP70, or HSP90), or a binding region-containing fragment thereof, has been established using any of the above methods, a compound that has substantially the same 3-D structure (or contains a domain that has substantially the same structure) as the binding region of the protein of interest can be produced. The compound's structure can be based on the 3-D structure of binding site of the parent protein (e.g., MUC1), the 3-D structure of the complementary acceptor site of the protein to which the parent protein binds (e.g., HSP70 or HSP90), or a combination of both. In this context, "has substantially the same 3-D structure" means that the compound binds with at least the same avidity as the parent protein to the non-parent partner. The compound can also bind to the non-parent partner with at least two-fold (at least: three-fold; four-fold; five-fold; six-fold; seven-fold; eight-fold; nine-fold; ten-fold; 20-fold; 50-fold; 100-fold; 1,000-fold; 10,000-fold; 100,000-fold; 1,000,000-fold; or even higher-fold) greater avidity than the parent protein. One of skill in the art would know how to test a compound for such an ability.

With the above described 3-D structural data on hand and knowing the chemical structure (e.g., amino acid sequence in the case of a protein) of the protein region of interest, those of skill in the art would know how to make compounds with the above-described properties. Such methods include chemical synthetic methods and, in the case of proteins, recombinant methods (see above). For example, cysteine residues appropriately placed in a compound so as to form disulfide bonds can be used to constrain the compound or a domain of the compound in an appropriate 3-D structure. In addition, in a compound that is a polypeptide or includes a domain that is a polypeptide, one of skill in the art would know what amino acids to include and in what sequence to include them in order to generate, for example, α-helices, β structures, or sharp turns or bends in the polypeptide backbone.

Of particular interest as small molecule compounds are nucleic acid aptamers which are relatively short nucleic acid (DNA, RNA or a combination of both) sequences that bind with high avidity to a variety of proteins and inhibit the binding to such proteins of ligands, receptors, and other molecules. Aptamers are generally about 25-40 nucleotides in length and have molecular weights in the range of about 18-25 kDa. Aptamers with high specificity and affinity for targets can be obtained by an in vitro evolutionary process termed SELEX (systemic evolution of ligands by exponential enrichment) (see, for example, Zhang et al. (2004) Arch. Immunol. Ther. Exp. 52:307-315, the disclosure of which is incorporated herein by reference in its entirety). For methods of enhancing the stability (by using nucleotide analogs, for example) and enhancing in vivo bioavailability (e.g., in vivo persistence in a subject's circulatory system) of nucleic acid aptamers see Zhang et al. (2004) and Brody et al. (2000) Reviews in Molecular Biotechnology 74:5-13, the disclosure of which is incorporated herein by reference in its entirety.

While not essential, computer-based methods can be used to design the compounds of the invention. Appropriate computer programs include: LUDI (Biosym Technologies, Inc., San Diego, Calif.), Aladdin (Daylight Chemical Information Systems, Irvine, Calif.); and LEGEND (Nishibata et al. (1985) J. Med. Chem. 36:2921-2928).

The compounds of the invention can include, in addition to the above described domains, one or more domains that facilitate purification (e.g., poly-histidine sequences) or domains that serve to direct the compound to appropriate target cells (e.g., cancer cells), e.g., ligands or antibodies (including antibody fragments such as Fab, F(ab')$_2$, or single chain Fv fragments) specific for cell surface components of target cells of the immune system, e.g., MUC1, Her2/Neu, or any of a variety of other tumor-associated antigens (TAA). Signal sequences that facilitate transport of the compounds across biological membranes (e.g., cell membranes and/or nuclear membranes) and/direct them to subcellular compartments can also be linked (e.g., covalently) to the compounds. Signal sequences are described in detail in U.S. Pat. No. 5,827,516, the disclosure of which is incorporated herein by reference in its entirety. All that is required in such multidomain compounds is that the domain corresponding to the parent inhibitory compound substantially retains the 3-D structure it would have in the absence of the additional domains. Conjugation to make such multidomain compounds can be by chemical methods (e.g., Barrios et al. (1992) Eur. J. Immunol. 22:1365-1372, the disclosure of which is incorporated herein by reference in its entirety). Where the compound is a peptide, it can be produced as part of a recombinant protein, such as one that self-assembles into virus-sized particles (e.g., U.S. Pat. No. 4,918,166, the disclosure of which is incorporated herein by reference in its entirety) that display candidate binding peptides on the surface.

Compounds of the invention that are peptides also include those described above, but modified for in vivo use by the addition, at the amino- and/or carboxyl-terminal ends, of a blocking agent to facilitate survival of the relevant polypeptide in vivo. This can be useful in those situations in which the peptide termini tend to be degraded by proteases prior to cellular uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill.

Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the peptide compounds can be covalently or noncovalently coupled to pharmaceutically acceptable "carrier" proteins prior to administration.

Compounds of the invention that are peptides can also include those described above, but modified by phosphorylation on a tyrosine residue. In place of a phosphate, the modification may utilize a phosphate mimic, such as tungstate, cacodylate, or sulfate.

Also of interest are peptidomimetic compounds that are designed based upon the amino acid sequences of compounds of the invention that are peptides. Peptidomimetic compounds are synthetic compounds having a three-dimensional conformation (i.e., a "peptide motif") that is substantially the same as the three-dimensional conformation of a selected peptide. The peptide motif provides the peptidomimetic compound with the ability to inhibit the interaction between MUC1 and a MUC1-binder. Peptidomimetic compounds can have additional characteristics that enhance their in vivo utility, such as increased cell permeability and prolonged biological half-life. The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

The proteins (MUC1, HSP70, or HSP90) used for designing compounds of the invention can be purified from natural sources (e.g., from tissues such as pancreas, liver, lung, breast, skin, spleen, ovary, testis, muscle, joint tissue, neural tissue, gastrointestinal tissue or tumor tissue (e.g., breast cancer or colon cancer tissue), or body fluids such as blood, serum, or urine). Smaller peptides (fewer than 100 amino acids long) and other non-protein compounds of the invention can be conveniently synthesized by standard chemical means known to those in the art. In addition, both polypeptides and peptides can be manufactured by standard in vitro recombinant DNA techniques and in vivo transgenesis using nucleotide sequences encoding the appropriate polypeptides or peptides. Methods well-known to those skilled in the art can be used to construct expression vectors containing relevant coding sequences and appropriate transcriptional/translational control signals. See for example, the techniques described in Sambrook et al., *Molecular Cloning: A Laboratory Manual* (2nd Ed.) (Cold Spring Harbor Laboratory, N.Y., 1989), and Ausubel et al., *Current Protocols in Molecular Biology* (Green Publishing Associates and Wiley Interscience, N.Y., 1989).

For the structural (e.g., x-ray crystallographic and NMR) analyses described above, it is generally required that proteins, or fragments thereof, be highly purified. Methods for purifying biological macromolecules (e.g., proteins) are known in the art. The degree of purity of proteins can be measured by any appropriate method, e.g., column chromatography, polyacrylamide gel electrophoresis, or HPLC analysis.

MUC1 and MUC1-binders used for the above analyses can be of any mammalian species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

Methods of Inhibiting Binding of MUC1 to a MUC1-Binder in a Cell

The invention features methods of inhibiting binding of MUC1 to a MUC1-binder (HSP70 or HSP90) in a cell, e.g., a cultured cell or an isolated cell. The method involves introducing into the cell a compound that inhibits the binding of a MUC1-binder to the MUC1 (e.g., to the MUC1 CD). Prior to introduction of the compound into the cell, the cell (or another cancer cell from the subject from which the cell to be treated was obtained) can optionally be tested for MUC1 expression. This can be done by testing for expression of either MUC1 protein or MUC1 mRNA by any of a wide variety of methods known in the art.

The compound can be one identified by the methods described above. Examples of appropriate compounds include the CD of human MUC1 (SEQ ID NO:1), peptide fragments of the CD of MUC1 that bind to MUC1-binders, and fragments of MUC1-binders that bind MUC1. An appropriate fragment of the CD of human MUC1 can be one containing or consisting of amino acids 46-72 (YEKVSAG-NGGSSLSYTNPAVAATSANL; SEQ ID NO:2) of the human MUC1 CD (SEQ ID NO:1). Other useful inhibitory compounds can be molecules that contain or consist of all or part of the substrate binding domains of human HSP70 (SEQ ID NO:3) and HSP90 (SEQ ID NO:4).

Peptide inhibitory compounds can contain up to 50 (e.g., one, two, three, four, five, six, seven, eight, nine, ten, 12, 15, 18, 20, 25, 30, 35, 40, 45, or 50) MUC1 or MUC1-binder residues or unrelated residues on either end or on both ends of the MUC1 or MUC1-binder inhibitory segments.

Any MUC1 or MUC1-binder peptides to be used as inhibitor compounds can optionally have any phosphorylation-susceptible amino acid residues phosphorylated, e.g., Tyr46 of SEQ ID NO:1.

Similarly HSP70 and HSP90 peptide fragment compounds will have substantially none of the mitochondrial localizing activity of HSP70 and HSP90 on MUC1. Compounds having substantially none of the mitochondrial localizing activity of HSP70 and HSP90 on MUC1 have less than 20% (e.g., less than: 10%; 5%; 2%; 1%; 0.5%; 0.2%; 0.1%; 0.01%; 0.001%; or 0.0001%) of the ability of HSP70 and/or HSP90 to localize MUC1 to mitochondria. Methods of designing, making, and testing such compounds for the appropriate binding-inhibitory activity are known to those in the art.

In addition, the inhibitory compounds can be antibodies, or antigen-binding antibody fragments, specific for MUC1, HSP70, or HSP90. Such antibodies will generally bind to, or close to: (a) the region of MUC1 to which HSP70 or HSP90 binds; (b) or the region on HSP70 or the region on HSP90 to which MUC1 binds (i.e., the substrate binding domain). However, as indicated above, the compounds can also act allosterically and so they can also bind to the three proteins at positions other than, and even remote from, the binding sites for MUC1 (on HSP70 and HSP90) and on HSP70 or HSP90 (for MUC1). As used throughout the present application, the term "antibody" refers to a whole antibody (e.g., IgM, IgG, IgA, IgD, or IgE) molecule that is generated by any one of a variety of methods that are known in the art. The antibody can be made in or derived from any of a variety of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

The antibody can be a purified or a recombinant antibody. Also useful for the invention are antibody fragments and chimeric antibodies and humanized antibodies made from non-human (e.g., mouse, rat, gerbil, or hamster) antibodies. As used herein, the term "antibody fragment" refers to an antigen-binding fragment, e.g., Fab, F(ab')$_2$, Fv, and single chain Fv (scFv) fragments. An scFv fragment is a single polypeptide chain that includes both the heavy and light chain variable regions of the antibody from which the scFv is derived. In addition, diabodies (Poljak (1994) Structure 2(12): 1121-1123; Hudson et al. (1999) J. Immunol. Methods 23(1-2): 177-189, the disclosures of both of which are incorporated herein by reference in their entirety) and intrabodies (Huston et al. (2001) Hum. Antibodies 10(3-4):127-142; Wheeler et al. (2003) Mol. Ther. 8(3):355-366; Stocks (2004) Drug Discov. Today 9(22): 960-966, the disclosures of all of which are incorporated herein by reference in their entirety) can be used in the methods of the invention.

Antibody fragments that contain the binding domain of the molecule can be generated by known techniques. For example: F(ab')$_2$ fragments can be produced by pepsin digestion of antibody molecules; and Fab fragments can be generated by reducing the disulfide bridges of F(ab')$_2$ fragments or by treating antibody molecules with papain and a reducing agent. See, e.g., National Institutes of Health, 1 *Current Protocols In Immunology*, Coligan et al., ed. 2.8, 2.10 (Wiley Interscience, 1991) the disclosure of which is incorporated herein by reference in their entirety. scFv fragments can be produced, for example, as described in U.S. Pat. No. 4,642,334, the disclosure of which is incorporated herein by reference in its entirety.

Chimeric and humanized monoclonal antibodies can be produced by recombinant DNA techniques known in the art, for example, using methods described in Robinson et al., International Patent Publication PCT/US86/02269; Akira et al., European Patent Application 184,187; Taniguchi, European Patent Application 171,496; Morrison et al., European Patent Application 173,494; Neuberger et al., PCT Application WO 86/01533; Cabilly et al., U.S. Pat. No. 4,816,567; Cabilly et al., European Patent Application 125,023; Better et al. (1988) Science 240, 1041-43; Liu et al. (1987) J. Immunol. 139, 3521-26; Sun et al. (1987) PNAS 84, 214-18; Nishimura et al. (1987) Canc. Res. 47, 999-1005; Wood et al. (1985) Nature 314, 446-49; Shaw et al. (1988) J. Natl. Cancer Inst. 80, 1553-59; Morrison, (1985) Science 229, 1202-07; Oi et al. (1986) BioTechniques 4, 214; Winter, U.S. Pat. No. 5,225, 539; Jones et al. (1986) Nature 321, 552-25; Veroeyan et al. (1988) Science 239, 1534; and Beidler et al. (1988) J. Immunol. 141, 4053-60. The disclosures of all these articles and patent documents are incorporated herein by reference in their entirety.

Cells to which the method of the invention can be applied include generally any cell that expresses MUC1. Such cells include normal cells, such as any normal epithelial cell, or a cancer cell, the proliferation of which it is desired to inhibit. An appropriate cancer cell can be a breast cancer, lung cancer, colon cancer; pancreatic cancer, renal cancer, stomach cancer; liver cancer, bone cancer, hematological cancer (e.g., leukemia or lymphoma), neural tissue cancel; melanoma, ovarian cancer, testicular cancer, prostate cancer, cervical cancer, vaginal cancer, or bladder cancer cell. In addition, the methods of the invention can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice.

The methods can be performed in vitro, in vivo, or ex vivo. In vitro application of appropriate compounds can be useful, for example, in basic scientific studies of tumor cell biology, e.g., studies on the mechanism of action of MUC1 and/or the MUC1-binders in promoting tumor cell growth, including survival. In addition, the compounds that are inhibitory can be used as "positive controls" in methods to identify additional compounds with inhibitory activity (see above). In such in vitro methods, cells expressing MUC1 and one or more of the MUC1-binders, can be incubated for various times with the inhibitory compound(s) at a variety of concentrations. Other incubation conditions known to those in art (e.g., temperature, or cell concentration) can also be varied. Inhibition of binding can be tested by methods such as those disclosed herein.

The methods of the invention will preferably be in vivo or ex vivo.

Compounds that inhibit binding between MUC1 and a MUC1-binder are generally useful as cancer cell (e.g., breast cancer cell) survival-inhibiting and/or cell cycle-arresting therapeutics or prophylactics. They can be administered to mammalian subjects (e.g., human breast cancer patients) alone or in conjunction with other drugs and/or radiotherapy. The compounds can also be administered to subjects that are genetically and/or due to, for example, physiological and/or environmental factors, susceptible to cancer, e.g., subjects with a family history of cancer (e.g., breast cancer), subjects with chronic inflammation or subject to chronic stress, or subjects that are exposed to natural or non-natural environmental carcinogenic conditions (e.g., excessive exposure to sunlight, industrial carcinogens, or tobacco smoke). As used herein, a compound that is "therapeutic" is a compound that causes a complete abolishment of the symptoms of a disease or a decrease in the severity of the symptoms of the disease. "Prevention" means that symptoms of the disease (e.g., cancer) are essentially absent. As used herein, "prophylaxis" means complete prevention of the symptoms of a disease, a delay in onset of the symptoms of a disease, or a lessening in the severity of subsequently developed disease symptoms.

When the methods are applied to subjects with cancer, prior to administration of a compound, the cancer can optionally be tested for MUC1 expression (MUC1 protein or MUC1 mRNA expression) by methods known in the art. In this way, subjects can be identified as having a MUC1-expressing cancer. Such methods can be performed in vitro on cancer cells obtained from a subject. Alternatively, in vivo imaging techniques using, for example, radiolabeled antibodies specific for MUC1 can be performed. In addition, body fluids (e.g., blood or urine) from subjects with cancer can be tested for elevated levels of MUC1 protein or MUC1 protein fragments.

In Vivo Approaches

In one in vivo approach, a compound that inhibits binding of MUC1 to a MUC1-binder is administered to a subject. Generally, the compounds of the invention will be suspended in a pharmaceutically-acceptable carrier (e.g., physiological saline) and administered orally or injected intravenously, subcutaneously, intramuscularly, intrathecally, intraperitoneally, intrarectally, intravaginally, intranasally, intragastrically, intratracheally, or intrapulmonarily. They can also be delivered directly to tumor cells, e.g., to a tumor or a tumor bed following surgical excision of the tumor, in order to kill any remaining tumor cells. The dosage required depends on the choice of the route of administration; the nature of the formulation; the nature of the patient's illness; the subject's size, weight, surface area, age, and sex; other drugs being administered; and the judgment of the attending physician. Suitable dosages are in the range of 0.0001 mg/kg-100 mg/kg. Wide variations in the needed dosage are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization as is well understood in the art. Administrations can be single or multiple (e.g., 2-, 3-, 4-, 6-, 8-, 10-, 20-, 50-, 100-, 150-, or more fold). Encapsulation of the polypeptide in a suitable delivery vehicle (e.g., polymeric microparticles or implantable devices) may increase the efficiency of delivery, particularly for oral delivery.

Alternatively, where an inhibitory compound is a polypeptide, a polynucleotide containing a nucleic acid sequence encoding the polypeptide can be delivered to appropriate cells in a mammal. Expression of the coding sequence can be directed to any cell in the body of the subject. However, expression will preferably be directed to cells in the vicinity of the tumor cells whose proliferation it is desired to inhibit. Expression of the coding sequence can be directed to the tumor cells themselves. This can be achieved by, for example, the use of polymeric, biodegradable microparticle or microcapsule delivery devices known in the art.

Another way to achieve uptake of the nucleic acid is using liposomes, prepared by standard methods. The vectors can be incorporated alone into these delivery vehicles or co-incorporated with tissue-specific or tumor-specific antibodies. Alternatively, one can prepare a molecular conjugate composed of a plasmid or other vector attached to poly-L-lysine by electrostatic or covalent forces. Poly-L-lysine binds to a ligand that can bind to a receptor on target cells (Cristiano et al. (1995) J. Mol. Med. 73:479, the disclosure of which is incorporated herein by reference in its entirety). Alternatively, tissue specific targeting can be achieved by the use of tissue-specific transcriptional regulatory elements (TRE) which are known in the art. Delivery of "naked DNA" (i.e., without a delivery vehicle) to an intramuscular, intradermal, or subcutaneous site is another means to achieve in vivo expression.

In the relevant polynucleotides (e.g., expression vectors), the nucleic acid sequence encoding the polypeptide of interest with an initiator methionine and optionally a targeting sequence is operatively linked to a promoter or enhancer-promoter combination. Short amino acid sequences can act as signals to direct proteins to specific intracellular compartments. Such signal sequences are described in detail in U.S. Pat. No. 5,827,516, the disclosure of which is incorporated herein by reference in its entirety.

Enhancers provide expression specificity in terms of time, location, and level. Unlike a promoter, an enhancer can function when located at variable distances from the transcription initiation site, provided a promoter is present. An enhancer can also be located downstream of the transcription initiation site. To bring a coding sequence under the control of a promoter, it is necessary to position the translation initiation site of the translational reading frame of the peptide or polypeptide between one and about fifty nucleotides downstream (3') of the promoter. Promoters of interest include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors, the adenoviral E1b minimal promoter, or the thymidine kinase minimal promoter. The DF3 enhancer can be particularly useful for expression of an inhibitory compound in cells that naturally express MUC1, for example, normal epithelial cells or malignant epithelial cells (carcinoma cells), e.g., breast cancer cells (see U.S. Pat. Nos. 5,565,334 and 5,874,415, the disclosures of which are incorporated herein by reference in their entirety). The coding sequence of the expression vector is operatively linked to a transcription terminating region.

Suitable expression vectors include plasmids and viral vectors such as herpes viruses, retroviruses, vaccinia viruses, attenuated vaccinia viruses, canary pox viruses, adenoviruses and adeno-associated viruses, among others.

Polynucleotides can be administered in a pharmaceutically acceptable carrier. Pharmaceutically acceptable carriers are biologically compatible vehicles that are suitable for administration to a human, e.g., physiological saline or liposomes. A therapeutically effective amount is an amount of the polynucleotide that is capable of producing a medically desirable result (e.g., decreased proliferation of cancer cells) in a treated animal. As is well known in the medical arts, the dosage for any one patient depends upon many factors, including the patient's size, body surface area, age, the particular compound to be administered, sex, time and route of administration, general health, and other drugs being administered concurrently. Dosages will vary, but a preferred dosage for administration of polynucleotide is from approximately $10^6$ to approximately $10^{12}$ copies of the polynucleotide molecule. This dose can be repeatedly administered, as needed. Routes of administration can be any of those listed above.

Ex Vivo Approaches

An ex vivo strategy can involve transfecting or transducing cells obtained from the subject with a polynucleotide encoding a polypeptide that inhibit binding of MUC1 to a MUC1-binder. The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells. Such cells act as a source of the inhibitory polypeptide for as long as they survive in the subject. Alternatively, tumor cells, preferably obtained from the subject but potentially from an individual other than the subject, can be transfected or transformed by a vector encoding the inhibitory polypeptide. The tumor cells, preferably treated with an agent (e.g., ionizing irradiation) that ablates their proliferative capacity, are then introduced into the patient, where they secrete the polypeptide.

The ex vivo methods include the steps of harvesting cells from a subject, culturing the cells, transducing them with an expression vector, and maintaining the cells under conditions suitable for expression of the polypeptide that inhibits inhibit binding of MUC1 to a MUC1-binder or phosphorylation of MUC1 by a MUC1-binder. These methods are known in the art of molecular biology. The transduction step is accomplished by any standard means used for ex vivo gene therapy, including calcium phosphate, lipofection, electroporation, viral infection, and biolistic gene transfer. Alternatively, liposomes or polymeric microparticles can be used. Cells that have been successfully transduced can be selected, for example, for expression of the coding sequence or of a drug resistance gene. The cells may then be lethally irradiated (if desired) and injected or implanted into the patient.

In any of the above methods of inhibiting the interaction between MUC1 and a MUC1-binder and of inhibiting expression of MUC1, one or more agents (e.g., two, three, four, five, six, seven, eight, nine, ten, 11, 12, 15, 18, 20, 25, 30, 40, 50, 60, 70, 80, 100, or more) including, for example, inhibitory compounds, antisense oligonucleotides, siRNA, drugs, aptamers, or other small molecules (or vectors encoding them), can be used.

The above in vivo and ex vivo methods of inhibiting interactions between MUC1 and MUC1-binders and inhibiting expression of MUC1 can be used in conjunction with any of a variety of other cancer therapeutic/prophylactic regimens (e.g., chemotherapeutic, radiotherapeutic, biotherapeutic/prophylactic, and immunotherapeutic/prophylactic regimens). Of particular interest are regimens involving genotoxic (DNA-damaging) agents. Such agents include various forms of ionizing and non-ionizing radiation and a variety of chemotherapeutic compounds.

Non-ionizing radiation includes, for example, ultra-violet (UV) radiation, infra-red (IR) radiation, microwaves, and electronic emissions. The radiation employed in the methods of the invention is preferably ionizing radiation. As used herein, "ionizing radiation" means radiation composed of particles or photons that have sufficient energy or can produce sufficient energy by atomic nuclear interactions to produce ionization (gain or loss of electrons) of an atom. Ionizing radiation thus includes, without limitation, α-radiation, β-radiation, γ-radiation, or x-radiation. A preferred radiation is x-radiation.

Ionizing radiation causes DNA damage and cell killing generally in proportion to the dose administered. It has been indicated that the multiple biological effects induced by ionizing radiation are due either to the direct interaction of the radiation with DNA or to the formation of free radical species which lead to damage of DNA. These effects include gene mutations, malignant transformation, and cell killing.

External and internal means for delivering ionizing radiation to a target tissue or cell are known in the art. External sources include β or γ sources or linear accelerators and the like. Alternatively, ionizing radiation may be delivered, for example, by administering a radiolabeled antibody that is capable of binding to a molecule expressed on the surface of a carcinoma (e.g., MUC1 or Her2/neu) to a subject, or by implantation of radiation-emitting pellets in or near the tumor (brachytherapy).

The amount of radiation (e.g., ionizing radiation) needed to kill a given cell generally depends upon the nature of the cell. As used herein, an "effective dose" of radiation means a dose of radiation that produces cell damage or death when given in conjunction with an adenoviral vector of the invention. Means of determining an effective dose are known in the art. Dosage ranges for x-radiation range from daily doses of 50 to 200 roentgens for prolonged periods of time (e.g., 6-8 weeks or even longer) to single doses of 2,000 to 6,000 roentgens. Dosages for administered radioisotopes vary widely, and depend on the half-life of the isotope, the strength and type of radiation emitted, and the degree of uptake by the target cells.

As used herein, "chemotherapeutic agents" are chemical compounds that are useful for inhibiting the growth, proliferation, or division of cancer cells, e.g., agents that enter cells and damage DNA, Thus, they can be compounds which, for example, directly cross-link DNA (e.g., cisplatin (CDDP) and other alkylating agents), intercalate into DNA, or interfere with DNA replication, mitosis, or chromosomal segregation, e.g., adriamycin (also known as doxorubicin), VP-16 (also known as etoposide), podophyllotoxin, and the like. These compounds are widely used in the treatment of carcinomas. Chemotherapeutic agents useful in the methods of the invention include, without limitation, cisplatin, carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide, podophyllotoxin, tamoxifen, taxol, transplatinum, 5-fluorouracil, vincristin, vinblastin, methotrexate, or any analog or derivative of these that is effective in damaging DNA.

Routes of administration are the same as those disclosed herein for interaction-inhibiting and expression-inhibiting compounds. Doses and frequency of administration vary widely according to all the variables listed above for administration of interaction-inhibiting and expression-inhibiting compounds. For example, adriamycin can be administered by bolus intravenous injection at doses in the range of 25-75 mg/kg and etoposide can be administered intravenously or orally at doses in the range of 35-100 mg/kg. Methods of determining optimal parameters of administration are well known in the art.

Combination treatments can include administration of one or more (e.g., one, two, three, four, five, six, seven, eight, nine or ten) interaction-inhibiting and/or expression-inhibiting compounds of the invention, and one or more (e.g., one, two, three, four, five, six, seven, eight, nine or ten) radiation modalities, and/or one or more (e.g., one, two, three, four, five, six, seven, eight, nine or ten) chemotherapeutic agents. The interaction-inhibiting and expression-inhibiting compounds, radiation treatments and chemotherapeutic agents can be given in any order and frequency. They can be given simultaneously or sequentially. Treatment with any one of the modalities (interaction-inhibiting and expression-inhibiting compounds, radiation, or chemotherapeutic agents) can involve single or multiple (e.g., two, three, four, five, six, eight, nine, ten, 12, 15, 20, 30, 40, 50, 60, 80, 100, 200, 300, 500, or more) administrations separated by any time period found to be optimal in terms of therapeutic benefit. Multiple administrations can be separated by one to 23 hours, a day, two, three days, four days, five days, six days, seven days, eight, ten days, twelve days, two weeks, three weeks four weeks, a month, two months, three months, four months, five months, six months, seven months, eight months, nine months, ten months, eleven months, a year, one and one half of a year, two years, three years, five years, or ten years. Administrations can be continued for as long as the subject is need of the treatment, e.g., any of the of the above time intervals, and can be for the life of the subject. Administrations can be, for example, once a week for the life-time of the subject. When administrations of any or all of the modalities are multiple, the course of any one can be simultaneous with, overlapping with, or consequent to the course(s) of the other(s).

The invention is illustrated, and not limited, by the following examples.

EXAMPLES

Example 1

Materials and Methods

Cell culture. Human HCT116/vector, HCT116/MUC1, HCT116/MUC1(Y46F) (Ren et al. (2004) Cancer Cell 5:163-175) and HCT116/MUC1-CD (Huang et al. (2003) Cancer Biol. Ther. 2:702-706) cells were cultured in Dulbecco's Modified Eagle Medium/F12 with 10% heat-inactivated fetal bovine serum (HI-FBS), 100 units/ml penicillin, 100 mg/ml streptomycin, and 2 mM L-glutamine. Human HeLa cervical carcinoma, 293 embryonic kidney and MCF-7 breast cancer cells were grown in Dulbecco's Modified Eagle Medium containing 10% HI-FBS, antibiotics and L-glutamine. Human ZR-75-1 breast cancer cells were cultured in RPMI1640 medium containing 10% HI-FBS, antibiotics and L-glutamine. Cells were grown to 60% confluence and then maintained overnight in medium with 0.1% serum before treatment with heregulin (HRG; 20 ng/ml; Calbiochem-Novabiochem, LaJolla, Calif.). Cells were also treated with PP2 (10 μM; Calbiochem-Novabiochem) or geldanamycin (GA; 1 μM; Calbiochem-Novabiochem).

Tandem affinity purification of MUC1 protein complexes. The procedure for purification and analysis of intracellular protein complexes has been described (Ogawa et al. (2002) Science 296:1132-6; Shi et al. (2003) Nature 422:735-8). In brief, MUC1-C was cloned downstream to HA and Flag tags in the retroviral pOZ-N vector (Nakatani and Ogryzko (2003) Methods Enzymol. 370:430-444), which expresses the IL-2 receptor (FIG. 1A). HeLa cells were transduced with retroviruses expressing MUC1 or the empty control vector and selected with IL-2-coupled magnetic beads. Intracellular protein complexes were purified by affinity chromatography using anti-Flag conjugated to beads. The adsorbed proteins were separated by centrifugation in 10-40% glycerol gradients. The gradient fractions reactive by immunoblotting with anti-Flag were subjected to electrophoresis in 4-20% polyacrylamide/SDS gels and stained with Coomassie blue. Proteins bands were excised and analyzed by MALDI-TOF-MS.

Immunoprecipitation and immunoblotting. Equal amounts of protein from cell lysates were incubated with anti-MUC1-N (antibody DF3) (Kufe et al. (1984) Hybridoma 3:223-232), anti-Flag (Sigma-Aldrich, St. Louis, Mo.), anti-c-Src (Upstate Biotechnology, Lake Placid, N.Y.), anti-HSP90 (BD Biosciences PharMingen, San Diego, Calif.) or normal mouse IgG (Santa Cruz Biotechnology, Santa Cruz, Calif.) for 2 hours at 4° C. Immune complexes were prepared as described (Li et al. (1998) Mol. Cell. Biol. 18:7216-7224) and subjected to immunoblot analysis with anti-HSP70, anti-HSP90, anti-MUC1-N, anti-MUC1-C (Ab5; Neomarkers, Fremont, Calif.), anti-phospho-c-Src(Tyr416) (Cell Signaling Technology, Beverly, Mass.) or anti-c-Src. Lysates not subjected to immunoprecipitation were immunoblotted with anti-MUC1-C, anti-HSP60 (Stressgen Biotechnologies, Victoria, BC, Canada), anti-PDGFR (Santa Cruz Biotechnology), anti-BAP31 (Abcam, Cambridge, Mass.), anti-PCNA (Calbiochem-Novabiochem), anti-IkBa (Santa Cruz Biotechnology), anti-calreticulin (Stressgen Biotechnologies), anti-Tom20 (BD Biosciences), anti-Tim23 (BD Biosciences), anti-Tim44 (BD Biosciences) or anti-β-actin (Sigma-Aldrich). Reactivity was detected with horseradish peroxidase-conjugated secondary antibodies and chemiluminescence (PerkinElmer Life Sciences, Boston, Mass.). Intensity of the signals was determined by densitometric scanning. Statistical significance was determined by the Student's t-test.

Cell transfections. 293 cells were transiently transfected with pIRES-puro2-MUC1, pIRES-puro2-MUC1(Y46F), or pCMV-c-Src (Li et al. (2001) J. Biol. Chem. 276:6061-6064) in the presence of LipofectAMINE™ (Invitrogen Life Technologies, Carlsbad, Calif.).

Binding Studies. Sequences encoding MUC1-CD, MUC1-CD(1-45), or MUC1-CD(46-72) were amplified by PCR and cloned into the pGEX-4T vector (Amersham Biosciences, Piscataway, N.J.). Purified GST-MUC1-CD fusion proteins bound to glutathione beads were incubated with purified recombinant human HSP70 or HSP90 (Stressgen Biotechnologies) for 1 hour at 4° C. In other experiments, the purified GST fusion proteins bound to glutathione beads were incubated with or without 50 ng c-Src (Upstate Biotechnology) in the presence of 200 mM ATP for 20 minutes at 30° C. HSP90 was then added for 1 hour at 4° C. Precipitated proteins were subjected to immunoblot analysis with anti-HSP70 or anti-HSP90.

Subcellular fractionation. Cell membranes and mitochondria were purified as described (Kharbanda et al. (1996) Cancer Res. 56:3617-3621; Ren et al. (2004) Cancer Cell 5:163-175). Cytosolic fractions were purified as described (Datta et al. (2000) J. Biol. Chem. 275:31733-31738; Kharbanda et al. (1996) Cancer Res. 56:3617-3621). The mitochondria (200 mg) were suspended in 40 ml SM buffer (10 mM MOPS-KOH, pH 7.2, 250 mM sucrose) and then divided into two equal aliquots (Ryan et al. (2001) Methods Cell Biol. 65:189-215). SM buffer (180 ml) was added to one aliquot, and hypotonic buffer (10 mM MOPS-KOH, pH 7.2; 180 ml) was added to the other aliquot. The samples were incubated for 15 minutes on ice and then left untreated or digested with 60 mg/ml trypsin (Sigma-Aldrich) for 15 minutes at 4° C. In other experiments, purified mitochondria in suspension buffer (5 mM HEPES, pH 7.4, 210 mM mannitol, 70 mM sucrose, 100 mM KCl, and 1 mM EGTA) were treated with 0.5% or 1% digitonin (Sigma-Aldrich) for 15 minutes at 4° C. Alternatively, the mitochondria were incubated with 0.5% digitonin for 1 minute at 4° C., diluted with suspension buffer, and then treated with 60 mg/ml trypsin for 15 minutes at 4° C.

Example 2

Tandem Affinity Purification of MUC1 Protein Complexes

Figure 1B:
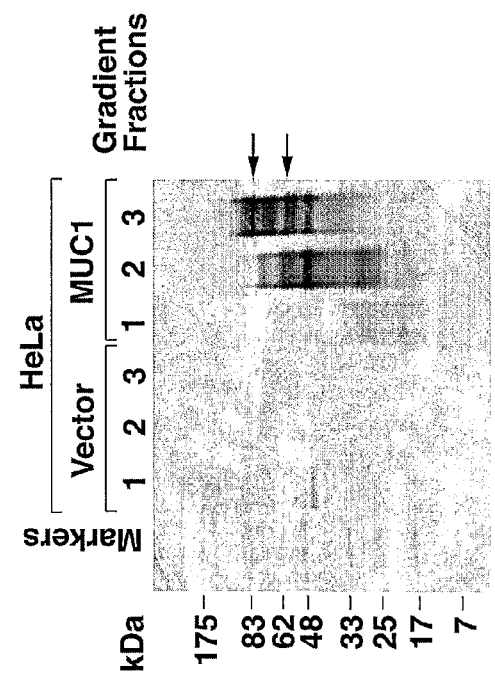
FIG. 1B is a reproduction of an SDS-PAGE gel of proteins purified from HeLa cells stably expressing pOZ-N-MUC1 (MUC1) or the empty vector (Control) by immunoprecipitation with anti-Flag and separation of the precipitated proteins by glycerol gradient centrifugation. Proteins in the corresponding gradient fractions were analyzed by SDS-PAGE and Coomassie blue staining. MUC1-associated proteins with apparent masses of 70 and 90 kDa are highlighted with arrows.

To identify proteins that associate with MUC1, MUC1-C was cloned downstream of Flag and HA tags in the retroviral pOZ-N vector (FIG. 1A). Lysates from HeLa cells stably transduced with the MUC1 retrovirus or the empty retrovirus were subjected to affinity chromatography with anti-Flag conjugated to beads. The adsorbed protein complexes were separated by glycerol gradient centrifugation. Analysis of Flag-positive gradient fractions by SDS-PAGE and Coomassie blue staining showed multiple proteins that associated with MUC1 (FIG. 1B). Identification of two MUC1-associated proteins with molecular masses of ~70 and 90 kDa was determined by MALDI-TOF-MS. Mass fingerprinting and sequencing of selected peptides demonstrated identity of the smaller protein with HSP70 (FIG. 1C). The other protein was identified as HSP90 (FIG. 1D). By contrast, HSP70 and HSP90 were undetectable following the same analysis of proteins immunoprecipitated with anti-Flag from cells expressing the empty retroviral vector. These findings indicated that MUC1 forms intracellular complexes with the HSP70 and HSP90 chaperones.

Example 3

MUC1 Binds to HSP70 and HSP90

To confirm the association of MUC1 with HSP70 and HSP90, lysates from HCT116 cells that stably express MUC1 were immunoprecipitated with anti-MUC1-N or a control IgG. Immunoblot analysis of the precipitates with anti-HSP70 or anti-HSP90 confirmed that MUC1 forms complexes with both chaperones (FIG. 2A). Intensity of the HSP70 and HSP90 signals, as determined by scanning densitometry, indicated that MUC1 associated with approximately 0.6% and 0.4% of the total HSP70 and HSP90 pools, respectively. To determine if the MUC1 cytoplasmic domain (MUC1-CD) confers the association with HSP70 and/or HSP90, lysates from HCT116 cells stably expressing Flag-MUC1-CD were immunoprecipitated with anti-Flag. Immunoblot analysis of the precipitates demonstrated that MUC1-CD associates with both HSP70 and HSP90 (FIG. 2B). To investigate whether MUC1 interacts directly with HSP70 or HSP90, GST or GST-MUC1-CD was incubated with purified recombinant HSP proteins (FIG. 2C). Immunoblot analysis of the adsorbates showed that MUC1-CD binds to HSP70, but not HSP90 (FIG. 2D). When deletion mutants of MUC1-CD were used in similar reactions, binding to HSP70 was detected with MUC1-CD(46-72), but not MUC1-CD(1-45) (FIG. 2D), indicating that the C-terminal region of MUC1-CD confers the interaction.

Figure 2E:
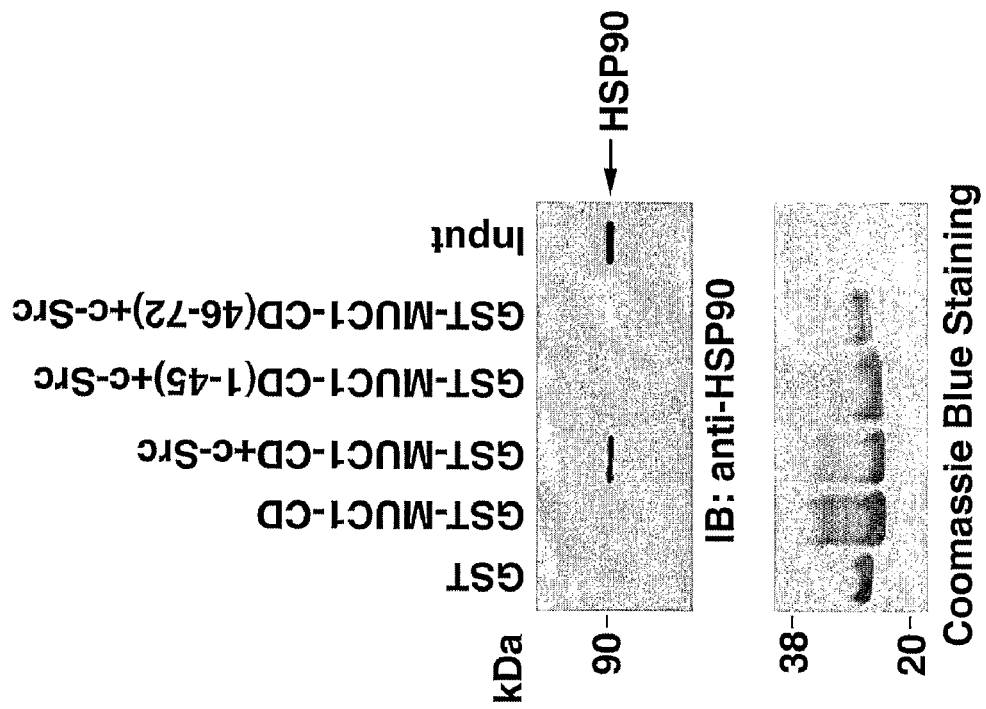
FIG. 2E is a series of immunoblots of HSP90 binding to MUC1-CD. The indicated GST-MUC1-CD fusion proteins were incubated with c-Src and ATP for 20 minutes at 30° C. HSP90 was then added for 1 hour at 4° C. The adsorbates were analyzed by immunoblotting with anti-HSP90. Loading of the GST proteins was assessed by Coomassie blue staining.

MUC1 is phosphorylated on Y-46 by c-Src and the pYEKV motif functions as a binding site for the c-Src SH2 domain (Li et al. (2001) J. Biol. Chem. 276:6061-6064) (FIG. 2C). To determine if c-Src regulates binding of MUC1-CD to HSP70 or HSP90, MUC1 was incubated with c-Src and ATP, and then the recombinant HSPs were added for binding reactions at 4° C. c-Src had little, if any, effect on binding of MUC1-CD and HSP70. However, c-Src induced binding of MUC1-CD to HSP90 (FIG. 2E). As a control, there was no detectable binding of HSP90 to the GST-MUC1-CD(1-45) deletion mutant (FIG. 2E). Moreover, there was no detectable binding of HSP90 to GST-MUC1-CD(46-72) which is phosphorylated by c-Src, suggesting that the sequences surrounding the MUC1 Y-46 site are of importance for the interaction with HSP90 (FIG. 2E). Of note, binding of MUC1-CD to HSP90 was performed in the absence of HSP70, indicating that HSP70 was dispensable for the MUC1-HSP90 interaction in vitro. These findings indicate that MUC1-CD binds directly to HSP70 and that binding of MUC1-CD to HSP90 in vitro is mediated by a c-Src-dependent mechanism.

Example 4

Figure 3B:
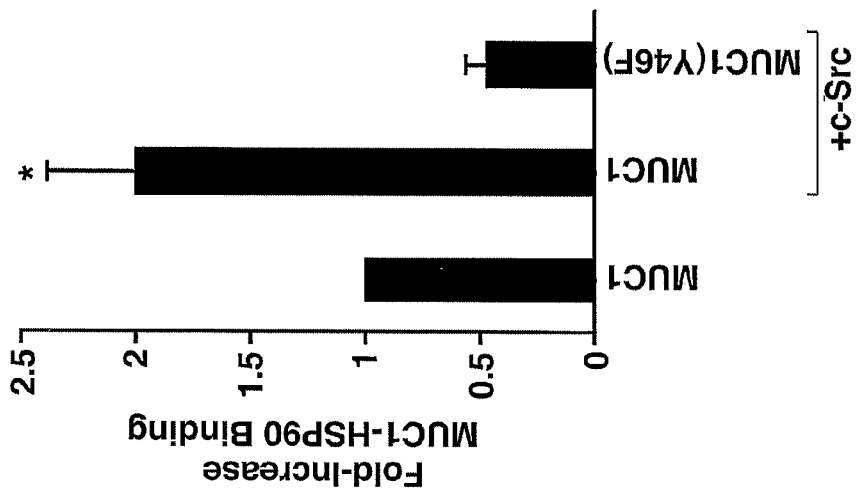
FIG. 3B is a bar graph depicting the intensities of the signals in FIG. 3B as assessed by densitometric scanning. The fold-increase in MUC1-HSP90 binding is expressed as the mean±SEM of three separate experiments compared to that obtained with the MUC1 control (assigned a value of 1). The asterisk denotes $p<0.05$ as compared to control.
Figure 3A:
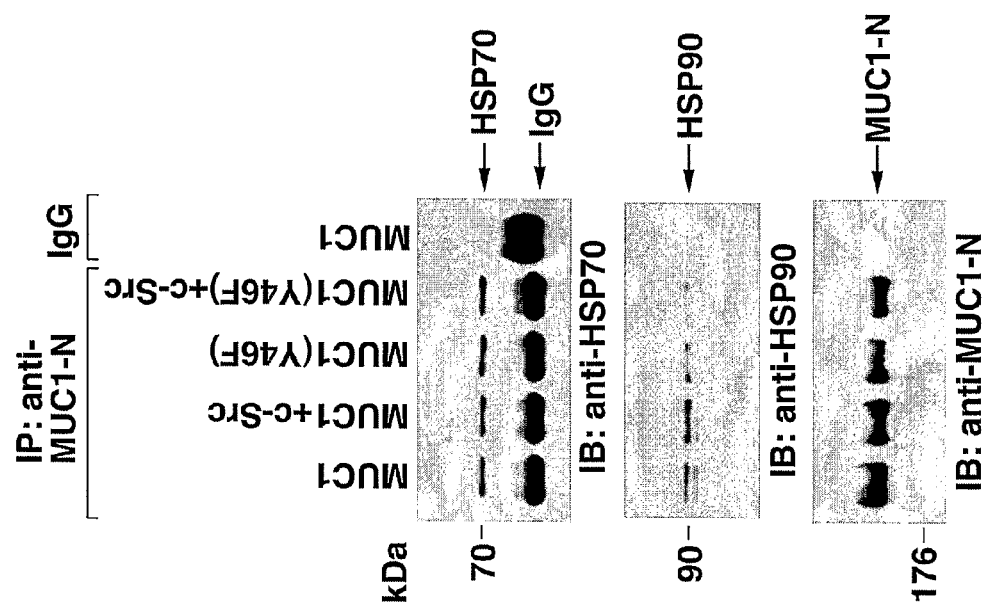
FIG. 3A is a series of immunoblots of immunoprecipitated lysates of 293 cells transiently transfected with MUC1 or MUC1(Y46F) in the presence and absence of c-Src. Anti-MUC1-N and control IgG immunoprecipitates were immunoblotted with the indicated antibodies.

Activation of c-Src and Phosphorylation of MUC1 on Y-46 Confers Binding to HSP90 In Vivo When MUC1 was expressed in 293 cells in the absence or presence of c-Src, there was little effect of c-Src on binding of MUC1 to HSP70 (FIG. 3A). Moreover, expression of MUC1 with a Y46F mutation had no apparent effect on binding of MUC1 to HSP70 in the absence or presence of c-Src (FIG. 3A). By contrast, c-Src stimulated binding of MIC1 to HSP90, and the Y46F mutation attenuated this response (FIG. 3A). These findings were confirmed in repeated experiments (FIG. 3B). As determined by autophosphorylation, HRG activated c-Src in HCT116/MUC1 cells (FIG. 3C). In addition, treatment of the HCT116/MUC1 cells with PP2, a c-Src inhibitor, blocked HRG-induced c-Src activation (FIG. 3C). Consequently, it was examined if HRG regulates binding of MUC1 to HSP90. Indeed, HRG stimulation of the HCT116/MUC1 cells was associated with an increase in binding of MUC1 and HSP90 (FIG. 3D). Consistent with involvement of c-Src, PP2 attenuated this response (FIG. 3D). As a control, inhibition of HSP90 with geldanamycin (GA), an inhibitor of HSP90 function (Whitesell et al. (1994) Proc. Natl. Acad. Sci. USA 91:8324-8), also attenuated the HRG-induced interaction between MUC1 and HSP90 (FIG. 3D). Similar results were obtained in repeated experiments (FIG. 3E). To confirm these results and further assess involvement of the Y-46 site, anti-HSP90 precipitates from control and HRG-treated HCT116/MUC1 cells were immunoblotted for MUC1. The results show that HRG increased the formation of MUC1-HSP90 complexes (FIG. 3F). As a control, MUC1 was not detectable in anti-HSP90 immunoprecipitates from HCT116/vector cells (FIG. 3F). Previous work has shown that HCT116 cells stably express similar levels of wild-type MUC1 and MUC1(Y46F) (Ren et al. (2004) Cancer Cell 5:163-175). Notably, the interaction between MUC1 and HSP90 was attenuated by the MUC1 Y46F mutation in control and HRG-treated cells (FIG. 3F). HRG-induced binding of MUC1 to HSP90, and attenuation of this response with MUC1 (Y46F) was confirmed in repeated experiments (FIG. 3G). These findings indicate that activation of c-Src by HRG, and thereby phosphorylation of MUC1 on Y-46, stimulates the interaction between MUC1 and HSP90.

Example 5

HRG Induces Binding of Endogenous MUC1 and HSP90

To determine if HRG also stimulates binding of endogenous MUC1 and HSP90, lysates from human MCF-7 breast cancer cells were immunoprecipitated with anti-MUC1-N. Immunoblot analysis of the precipitates demonstrated that endogenous MUC1 associates with HSP70 and that HRG has little if any effect on this interaction (FIGS. 4A and 4B). Moreover, as found in HCT116/MUC1 cells, stimulation of MCF-7 cells with HRG was associated with increased binding of MUC1 and HSP90 (FIGS. 4A and 4B). In the reciprocal experiment, immunoblot analysis of anti-HSP90 precipitates with anti-MUC1-C confirmed that HRG stimulates binding of MUC1-C and HSP90 (FIGS. 4C and 4D). Studies with human ZR-75-1 breast cancer cells that express endogenous MUC1 also demonstrated that HRG has no apparent effect on the constitutive interaction between MUC1 and HSP70 (FIGS. 4E and 4F). However, as found in MCF-7 cells, HRG stimulation was associated with increased binding of MUC1 and HSP90 (FIGS. 4E and 4F). These results were confirmed when anti-HSP90 precipitates from control and HRG-stimulated ZR-75-1 cells were immunoblotted with anti-MUC1-C (FIGS. 4G and 4H). These findings indicate that HRG stimulates the interaction between endogenous MUC1 and HSP90, but not HSP70.

Example 6

HRG Stimulates Binding of MUC1 to HSP90 at the Cell Membrane and in the Cytosol

MUC1 is a cell membrane-associated protein that also accumulates in the cytosol of transformed cells (Croce et al. (2003) J. Histochem. Cytochem. 51:781-8; Kufe et al. (1984) Hybridoma 3:223-232; Perey et al. (1992) Cancer Res. 52:2563-3568; Rahn et al. (2001) Cancer 91:1973-82). To assess the subcellular location where MUC1 interacts with HSP90, whole cell lysates and purified cell membranes from control and HRG-stimulated HCT116/MUC1 cells were immunoprecipitated with anti-MUC1-N. Immunoblot analysis of the precipitates with anti-HSP90 showed that, as found for whole cell lysates, HRG stimulates binding of MUC1 and HSP90 at the cell membrane (FIGS. 5A and 5B). HRG stimulation was also associated with an increase in cytosolic MUC1-C levels (FIGS. 5C and 5D). The purity of the cytosolic fraction was confirmed by immunoblotting with antibodies against the cell membrane-associated platelet-derived growth factor receptor (PDGFR), endoplasmic reticulum (ER)-associated BAP31 (Ng et al. (1997) J. Cell. Biol. 139: 327-38), and the mitochondria-associated Tom20 proteins (FIGS. 5C and 5D). In concert with these results, it was also found that HRG increases binding of cytosolic MUC1-C and HSP90 (FIGS. 5E and 5F). To confirm that HRG stimulates binding of cytosolic MUC1 to HSP90, HCT116 cells were studied that stably express Flag-MUC1-CD, which is devoid of the transmembrane domain and is expressed in the cytosol (Huang et al. (2003) Cancer Biol. Ther. 2:702-706). HRG stimulation of the HCT116/MUC1-CD cells had little effect on binding of MUC1-CD to HSP70 (FIGS. 5G and 5H). However, like full-length MUC1, HRG stimulated binding of MUC1-CD to HSP90 (FIGS. 5G and 5H), confirming that cytosolic MUC1 formed a complex with HSP90. These findings indicate that HRG stimulates binding of MUC1 to HSP90 at the cell membrane and in the cytosol.

Example 7 c-Src and HSP90 Regulate Delivery of MUC1 to Mitochondria

Figure 6A:
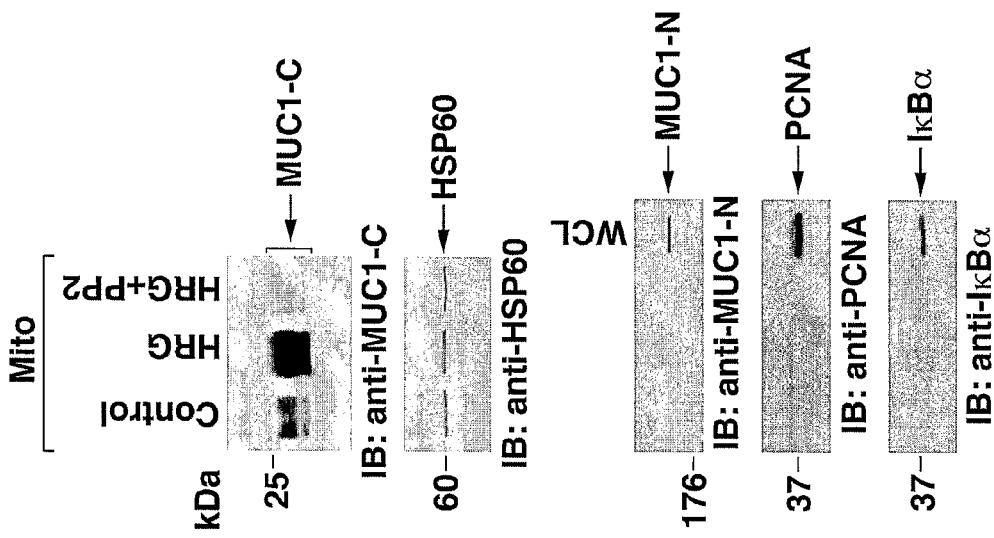
FIG. 6A is a series of immunoblots of purified mitochondria from HCT116/MUC1 cells that were treated with HRG for 10 minutes or with PP2 for 1 hour and then HRG. Purified mitochondria were subjected to immunoblotting with the indicated antibodies. Whole cell lysate (WCL) was included as a control. The amount of WCL loaded in the lane represents 0.06% of the total protein used to purify the mitochondrial fraction.
Figure 6B:
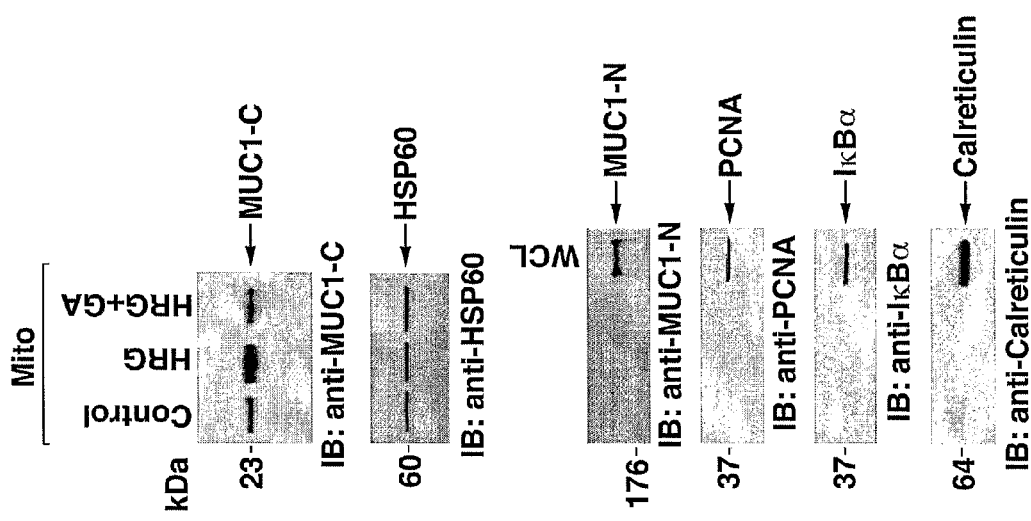
FIG. 6B is a series of immunoblots of purified mitochondria from HCT116/MUC1 cells that were treated with HRG for 10 minutes or with GA for 1 hour and then HRG. Purified mitochondria were subjected to immunoblotting with the indicated antibodies. Whole cell lysate (WCL) was included as a control. The amount of WCL loaded in the lane represents 0.06% of the total protein used to purify the mitochondrial fraction.

HRG stimulation is associated with targeting of MUC1-C to mitochondria (Ren et al. (2004) Cancer Cell 5:163-175). To assess the involvement of c-Src in mitochondrial targeting of MUC1-C, mitochondria were purified from HCT116/MUC1 cells stimulated with HRG in the absence and presence of PP2. The results confirm that HRG induces localization of MUC1-C, and not MUC1-N, to mitochondria and show that this response is attenuated by PP2 (FIG. 6A). Equal loading of the mitochondrial lysates was confirmed by immunoblotting for the mitochondrial HSP60 protein (FIG. 6A). Densitometric scanning of the constitutive mitochondrial MUC1-C signal indicated that 0.5 to 1% of total cellular MUC1-C localized to the mitochondria. Treatment with GA also blocked HRG-induced targeting of MUC1 to mitochondria, consistent with the involvement of HSP90 in this response (FIG. 6B). In addition purity of the mitochondria was confirmed by immunoblotting with antibodies against the nuclear PCNA, cytosolic IκBα, and ER-associated calreticulin proteins (FIG. 6B). As an additional control, there was no detectable ErbB2 in the purified mitochondrial fraction. To assess stability of MUC1 that constitutively resides in mitochondria, HCT116/MUC1 cells were treated with GA for 4, 8, and 16 hours (FIG. 6C). Decreases in mitochondrial MUC1 levels were detectable with GA exposures of 8 and 16 hours (FIG. 6C). Densitometric scanning of the signals indicated that GA decreases mitochondrial MUC1 with a half-life of approximately 8 hours. As a control, similar exposures to GA had little effect on total intracellular MUC1 levels (FIG. 6C). These findings indicate that MUC1 is targeted to mitochondria by a mechanism dependent on c-Src and HSP90.

Example 8

MUC1 is Integrated into the Mitochondrial Outer Membrane

Complexes of HSP70 and HSP90 function in the transport of proteins, such as MUC1, without N-terminal mitochondrial localization sequences to the mitochondrial surface (Young et al. (2003) Cell 112:41-50). Previous work has demonstrated that mitochondrial MUC1 is an integral membrane protein that is resistant to trypsin digestion (Ren et al. (2004) Cancer Cell 5:163-175). To further define the localization of MC1, purified mitochondria were incubated in hypotonic buffer to induce swelling and disruption of the outer membrane (FIG. 7A). As shown previously (Ren et al. (2004) Cancer Cell 5:163-175), treatment of mitochondria with trypsin had no effect on MUC1 but decreased Tom20, a component of the translocase of the outer membrane (FIG. 7A). Of note, the N-terminus of Tom20 is anchored in the mitochondrial outer membrane and, as such, the Tom20 C-terminal region is susceptible to protease digestion. Trypsin digestion had no apparent effect on Tim23, a component of the mitochondrial inner membrane (FIG. 7A). After hypotonic disruption of the outer membrane, trypsin treatment had no effect on MUC1, but was associated with partial decreases in Tim23 levels and not the matrix HSP60 protein, consistent with access of the protease to the mitochondrial inner membrane (FIG. 7A). In this regard, the region of Tim23 recognized by anti-Tim23 extends into the intermembrane space from the surface of the mitochondrial inner membrane (Moro et al. (1999) EMBO J. 18:3667-75). To further assess the localization of MUC1, the mitochondrial outer membrane was permeabilized with digitonin. Treatment with 0.5 or 1.0% digitonin alone had no effect on MUC1 or mitochondrial proteins associated with the outer (Tom20) or inner (Tim23 and Tim44) membranes (FIG. 7B). However, treatment of the mitochondria with both digitonin and trypsin resulted in complete digestion of MUC1, Tom20 and Tim23 (FIG. 7C). By contrast, digitonin and trypsin had little effect on Tim44, a protein associated with matrix face of the mitochondrial inner membrane (FIG. 7C). These findings collectively indicate that MUC1 is embedded in the mitochondrial outer membrane.

REFERENCES

Baldus S E, Monig S P, Huxel S, Landsberg S, Hanisch F G, Engelmami K, Schneider P M, Thiele J, Holscher A H and Dienes H P. (2004). *Clin. Cancer Res.,* 10, 2790-6.
Belsches-Jablonski A P, Biscardi J S, Peavy D R, Tice D A, Romney D A and Parsons S J. (2001). *Oncogene*, 20, 1465-75.
Bukau B, Deuerling E, Pfund C and Craig E A. (2000). *Cell,* 101, 119-22.
Croce M V, Isla-Larrain M T, Rua C E, Rabassa M E, Gendler S J and Segal-Eiras A. (2003). *J. Histochem. Cytochem.,* 51, 781-8.
Datta R, Oki E, Endo K, Biedermann V, Ren J and Kufe D. (2000). *J. Biol. Chem.,* 275, 31733-31738.
Gendler S, Taylor-Papadimitriou J, Duhig T, Rothbard J and Burchell J A. (1988). *J. Biol. Chem.,* 263, 12820-12823.
Hartl F U and Hayer-Hartl M. (2002). *Science,* 295, 1852-8.
Huang L, Ren J, Chen D, Li Y, Kharbanda S and Kufe D. (2003). *Cancer Biol. Ther.,* 2, 702-706.
Kharbanda S, Saleem A, Yuan Z-M, Kraeft S, Weichselbaum R, Chen L B and Kufe D. (1996). *Cancer Res.,* 56, 3617-3621.
Kinlough C L, Poland P A, Bruns J B, Harkleroad K L and Hughey R P. (2004). *J. Biol. Chem.,* 279, 53071-7.
Kufe D, Inghirami G, Abe M, Hayes D, Justi-Wheeler H and Schlom J. (1984). *Hybridoma,* 3, 223-232.
Levitan F, Stern 0, Weiss M, Gil-Henn C, Ziv R, Prokocimer Z, Smorodinksy N, Rubinstein D and Wreschner D. (2005). *J. Biol. Chem.,* (in press).
Li Y, Bharti A, Chen D, Gong J and Kufe D. (1998). *Mol. Cell. Biol.,* 18, 7216-7224.
Li Y, Chen W, Ren J, Yu W, Li Q, Yoshida K and Kufe D. (2003). *Cancer Biol. Ther.,* 2, 187-193.
Li Y, Kuwahara H, Ren J, Wen G and Kufe D. (2001). *J. Biol. Chem.,* 276, 6061-6064.
Li Y, Liu D, Chen D, Kharbanda S and Kufe D. (2003). *Oncogene,* 22, 6107-6110.
Li Y, Ren J, Yu W—H, Li G, Kuwahara H, Yin L, Carraway K L and Kufe D. (2001). *J. Biol. Chem.,* 276, 35239-35242.
Li Y, Yu W—H, Ren J, Huang L, Kharbanda S, Loda M and Kufe D. (2003). *Mol. Cancer. Res.,* 1, 765-775.
Ligtenberg M J, Kruijshaar L, Buijs F, van Meijer M, Litvinov S V and Hilkens J. (1992). *J. Biol. Chem.,* 267, 6171-7.
Merlo G, Siddiqui J, Cropp C, Liscia D S, Lidereau R, Callahan R and Kufe D. (1989). *Cancer Res.,* 49, 6966-6971.
Moro F, Sirrenberg C, Schneider H C, Neupert W and Brunner M. (1999). *EMBO J.,* 18, 3667-75.
Ng F W, Nguyen M, Kwan T, Branton P E, Nicholson D W, Cromlish J A and Shore G C. (1997). *J. Cell. Biol.,* 139, 327-38.
Ogawa H, Ishiguro K, Gaubatz S, Livingston D M and Nakatani Y. (2002). *Science,* 296, 1132-6.
Park S J, Suetsugu S and Takenawa T. (2005). *EMBO J.,* 24, 1557-70.
Perey L, Hayes D F, Maimonis P, Abe M, OHara C and Kufe D W. (1992). *Cancer Res.,* 52, 2563-3568.
Rahn J J, Dabbagh L, Pasdar M and Hugh J C. (2001). *Cancer,* 91, 1973-82.
Ren J, Agata N, Chen D, Li Y, Yu W—H, Huang L, Raina D, Chen W, Kharbanda S and Kufe D. (2004). *Cancer Cell,* 5, 163-175.
Ren J, Li Y and Kufe D. (2002). *J. Biol. Chem.,* 277, 17616-17622.
Ryan M T, Voos W and Pfanner N. (2001). *Methods Cell Biol.,* 65, 189-215.
Schroeder J, Thompson M, Gardner M and Gendler S. (2001). *J. Biol. Chem.,* 276, 13057-13064.
Schroeder J A, Masri A A, Adriance M C, Tessier J C, Kotlarczyk K L, Thompson M C and Gendler S J. (2004). *Oncogene,* 23, 5739-47.
Shi Y, Sawada J, Sui G, Affar el B, Whetstine J R, Lan F, Ogawa H, Luke M P and Nakatani Y. (2003). *Nature,* 422, 735-8.
Siddiqui J, Abe M, Hayes D, Shani E, Yunis E and Kufe D. (1988). *Proc. Natl. Acad. Sci. USA,* 85, 2320-2323.

Truscott K N, Brandner K and Pfanner N. (2003). *Curr. Biol.*, 13, R326-37.

Vadlamudi R K, Sahin A A, Adam L, Wang R A and Kumar R. (2003). *FEBS Lett.*, 543, 76-80.

Wada J and Kanwar Y S. (1998). *Proc. Natl. Acad. Sci. USA*, 95, 144-9.

Wei X, Xu H and Kufe D. (2005). *Cancer Cell*, 7, 167-178.

Wen Y, Caffrey T, Wheelock M, Johnson K and Hollingsworth M. (2003). *J. Biol. Chem.*, 278, 38029-39.

Whitesell L, Mimnaugh E G, De Costa B, Myers C E and Neckers L M. (1994). *Proc. Natl. Acad. Sci. USA*, 91, 8324-8.

Yamamoto M, Bharti A, Li Y and Kufe D. (1997). *J. Biol. Chem.*, 272, 12492-12494.

Yin L and Kufe D. (2003). *J. Biol. Chem.*, 278, 35458-64.

Young J C and Hartl F U. (2000). *EMBO J.*, 19, 5930-40.

Young J C, Hoogenraad N J and Hartl F U. (2003). *Cell*, 112, 41-50.

Other Embodiments

A number of embodiments of the invention have been described. Nevertheless, it will be understood that various modifications may be made without departing from the spirit and scope of the invention. Accordingly, other embodiments are within the scope of the following claims.

---

What is claimed is:

1. A method of identifying a compound that inhibits binding of MUC1 to HSP90, the method comprising:
   (a) providing a MUC1 test agent comprising SEQ ID NO: 1;
   (b) providing a HSP90 test agent comprising SEQ ID NO: 4 and that binds to the MUC1 test agent;
   (c) contacting the MUC1 test agent with the HSP90 test agent in the presence of a test compound under conditions that permit the binding of the MUC1 test agent with the HSP90 test agent in absence of the test compound; and
   (d) determining whether the test compound inhibits binding of the MUC1 test agent to the HSP90 test agent.

2. The method of claim 1, wherein the contacting is carried out in a cell-free system.

3. The method of claim 1, wherein the contacting occurs in a cell.

4. The method of claim 1, wherein the HSP90 test agent is phosphorylated.

5. The method of claim 4, wherein the HSP90 test agent is phosphorylated by c-Src.

6. The method of claim 1, wherein the contacting is performed further in the presence of c-Src.

7. The method of claim 1, further comprising manufacturing the compound if the compound inhibits the interaction between MUC1 and HSP90.

* * * * *